(12) United States Patent
Ribaut et al.

(10) Patent No.: US 9,895,297 B2
(45) Date of Patent: Feb. 20, 2018

(54) MICROCAPSULES

(71) Applicant: TAKASAGO INTERNATIONAL CORPORATION, Tokyo (JP)

(72) Inventors: Tiphaine Ribaut, Paris (FR); Jonathan Warr, Paris (FR); Stuart Fraser, Cheshire (GB); Olivier Anthony, Paris (FR)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 44 days.

(21) Appl. No.: 14/908,343

(22) PCT Filed: Jul. 28, 2014

(86) PCT No.: PCT/JP2014/070410
§ 371 (c)(1),
(2) Date: Jan. 28, 2016

(87) PCT Pub. No.: WO2015/016369
PCT Pub. Date: Feb. 5, 2015

(65) Prior Publication Data
US 2016/0206522 A1    Jul. 21, 2016

(30) Foreign Application Priority Data

Jul. 29, 2013 (EP) .................................... 13306095

(51) Int. Cl.
| | |
|---|---|
| *A61K 8/11* | (2006.01) |
| *B01J 13/14* | (2006.01) |
| *C11D 3/50* | (2006.01) |
| *C11D 17/00* | (2006.01) |
| *A61K 8/81* | (2006.01) |
| *A61Q 13/00* | (2006.01) |
| *A61Q 1/14* | (2006.01) |
| *A61Q 5/02* | (2006.01) |
| *A61Q 19/10* | (2006.01) |

(52) U.S. Cl.
CPC .............. *A61K 8/11* (2013.01); *A61K 8/8152* (2013.01); *A61Q 13/00* (2013.01); *B01J 13/14* (2013.01); *C11D 3/505* (2013.01); *C11D 17/0039* (2013.01); *A61K 2800/412* (2013.01); *A61K 2800/56* (2013.01); *A61Q 1/14* (2013.01); *A61Q 5/02* (2013.01); *A61Q 19/10* (2013.01)

(58) Field of Classification Search
CPC .................................... B01J 13/14; A61K 8/11
See application file for complete search history.

(56) References Cited

U.S. PATENT DOCUMENTS

| | | |
|---|---|---|
| 6,849,591 B1 | 2/2005 | Boeckh et al. |
| 2007/0224899 A1* | 9/2007 | Dungworth .............. B01J 13/18 442/164 |
| 2009/0289216 A1 | 11/2009 | Jung et al. |
| 2010/0327216 A1 | 12/2010 | Jung et al. |
| 2012/0058929 A1 | 3/2012 | Laubender et al. |
| 2012/0112122 A1 | 5/2012 | Jung et al. |
| 2012/0177924 A1 | 7/2012 | Jung et al. |
| 2012/0283104 A1 | 11/2012 | Jung et al. |
| 2013/0164355 A1 | 6/2013 | Aussant et al. |

FOREIGN PATENT DOCUMENTS

| | | |
|---|---|---|
| CN | 101838375 A | 9/2010 |
| CN | 102066498 A | 5/2011 |
| CN | 102395423 A | 3/2012 |
| CN | 102471404 A | 5/2012 |
| CN | 102724869 A | 10/2012 |
| DE | 19932144 A1 | 1/2001 |
| EP | 2397120 A1 | 12/2011 |
| WO | 2005/105291 A1 | 11/2005 |
| WO | 2008/046839 A1 | 4/2008 |

OTHER PUBLICATIONS

Search Report dated Oct. 20, 2014, issued by the International Searching Authority in counterpart International Application No. PCT/JP2014/070410 (PCT/ISA/210).
Written Opinion dated Oct. 20, 2014, issued by the International Searching Authority in counterpart International Application No. PCT/JP2014/070410 (PCT/ISA/237).
Office Action dated Mar. 9, 2017, by the State Intellectual Property Office of P.R. China in counterpart Chinese Application No. 201480043049.3.
Office Action dated Oct. 19, 2017, issued by the State Intellectual Property Office of P.R. China in Chinese application No. 201480043049.3.

* cited by examiner

*Primary Examiner* — Arrie L Reuther
(74) *Attorney, Agent, or Firm* — Sughrue Mion, PLLC

(57) ABSTRACT

A novel microcapsule which is endowed for example with reduced leakage of encapsulated materials. The microcapsule contains one or more fragrances and is suitable for inclusion in non-edible consumer goods products, laundry products, personal care products and cosmetic products. The microcapsule can be obtained in an economic and efficient manner by polymerizing an emulsion so that emulsion droplets are encapsulated into a subsequently cured polymeric shell.

2 Claims, No Drawings

MICROCAPSULES

TECHNICAL FIELD

The present disclosure discloses a microcapsule which comprises a perfume composition enclosed within a polymeric shell, a process for the manufacture of that microcapsule as well as non-ingestible consumer products (such as household cleaners, laundry products, personal care products and cosmetic products) containing that microcapsule.

BACKGROUND ART

Microcapsules encapsulating hydrophobic materials such as fragrances may be added to complex liquid products presenting a wide pH range from basic (e.g. 12) to acid (e.g. 2). For example, common liquid household, laundry personal care and cosmetic products, such as fabric conditioners and antiperspirants, have typically an acidic pH whilst liquid laundry detergents and hard surface cleaners have typically an alkaline pH.

SUMMARY OF INVENTION

Technical Problem

Existing microcapsules may not display satisfactory pH-independent shell properties. When shell properties are not satisfactory unwanted high leakage levels, especially upon storage, and loss of microcapsule olfactive properties may occur. Shell properties are also an important parameter when designing microcapsule which should release their content only upon an appropriate release trigger (such as in the case of friction-sensitive capsules).

The present disclosure provides a microcapsule containing one or more fragrances which is suitable for inclusion in non-edible consumer goods products, laundry products, personal care products and cosmetic products. The microcapsule can be obtained in an economic and efficient manner by polymerizing an emulsion so that emulsion droplets are encapsulated into a subsequently cured polymeric shell.

Solution to Problem

The present disclosure discloses a microcapsule which comprises a perfume composition enclosed within a polymeric shell. The microcapsule is endowed with reduced leakage of the fragrance for example upon storage and especially upon storage in a liquid medium.

The instant disclosure also discloses microcapsules which may display pH-independent shell properties. This means for example that the microcapsules may display satisfactory shell properties in acid (e.g. from pH 2) and alkaline conditions (e.g. up to pH 12), as can be found in many liquid household, laundry personal care and cosmetic products, such as fabric conditioners and antiperspirants (acidic pH) or liquid laundry detergents and hard surface cleaners (alkaline pH). The instant disclosure also discloses a simple and effective process for the manufacture of a microcapsule as presently defined. The instant disclosure also discloses a product, such as a non-edible consumer goods product, a laundry product, a personal care product or a cosmetic product containing a microcapsule as presently defined. In particular, the present disclosure discloses for example the following points:

1. A microcapsule comprising a perfume composition enclosed within a polymeric shell, wherein:
   the perfume composition includes a fragrance, and
   the polymeric shell includes in polymerized form a blend including:
   i) between 40% and 70% by weight over the combined weight of compounds (I) and (II) in the blend of a compound (I) which is a combination of:
      ia) between 50% and 100% by weight over the weight of the combination of a neutral monomethacrylate monomer (Ia) having a solubility in water at pH 7 and 20° C. equal to, or more than 2 g/100 ml,
      ib) between 0% and 50% by weight over the weight of the combination of another neutral monoethylenically unsaturated monomer (Ib), and
      ic) between 0% and 15% by weight over the weight of the combination of a ionized or ionizable monoethylenically unsaturated monomer (Ic),
   ii) between 30% and 60% by weight over the combined weight of compounds (I) and (II) in the blend of a compound (II) which is a polyethylenically unsaturated monomer selected from the group consisting of divinylbenzene, trivinylbenzene, a $C_2$-$C_{24}$ alkyl di- or polyester of (meth)acrylic acid, a $C_2$-$C_{24}$ alkyl di- or polyamide of (meth)acrylic acid and mixtures thereof.

2. A microcapsule comprising a perfume composition enclosed within a polymeric shell, wherein:
   the perfume composition includes a fragrance, and
   the polymeric shell includes in polymerized form a blend including:
   i) between 40% and 70% by weight over the combined weight of compounds (I) and (II) in the blend of a compound (I) which is a combination of:
      ia) between 50% and 100% by weight over the weight of the combination of a neutral monomethacrylate monomer (Ia) having a solubility in water at pH 7 and 20° C. equal to, or more than 2 g/100 ml,
      ib) between 0% and 50% by weight over the weight of the combination of another neutral monoethylenically unsaturated monomer (Ib), and
      ic) between 0% and 15% by weight over the weight of the combination of a ionized or ionizable monoethylenically unsaturated monomer (Ic),
   ii) between 30% and 60% by weight over the combined weight of compounds (I) and (II) in the blend of a compound (II) which is a polyethylenically unsaturated monomer selected from the group consisting of divinylbenzene, trivinylbenzene, a $C_2$-$C_{24}$ alkyl di- or polyester of (meth)acrylic acid, a $C_2$-$C_{24}$ alkyl di- or polyamide of (meth)acrylic acid and mixtures thereof,
   wherein the compound (II) is such that the microcapsule provides for a fragrance leakage of less than about 60% when tested upon storage for 4 weeks at 40° C. in a test liquid base, according to a leakage test method, when the microcapsule is prepared according to a leakage test manufacturing procedure, and the microcapsule encapsulates fragrance no. 1, the test liquid base, the leakage test method, the leakage test manufacturing procedure and the fragrance no. 1 being as defined in the examples.

3. A microcapsule comprising a perfume composition enclosed within a polymeric shell, wherein:
   the perfume composition includes a fragrance, and
   the polymeric shell includes in polymerized form a blend including:

i) between 40% and 70% by weight over the combined weight of compounds (I) and (II) in the blend of a compound (I) which is a combination of:
   ia) between 50% and 100% by weight over the weight of the combination of a neutral monomethacrylate monomer (Ia) having a solubility in water at pH 7 and 20° C. equal to, or more than 2 g/100 ml,
   ib) between 0% and 50% by weight over the weight of the combination of another neutral monoethylenically unsaturated monomer (Ib), and
   ic) between 0% and 15% by weight over the weight of the combination of a ionized or ionizable monoethylenically unsaturated monomer (Ic),
ii) between 30% and 60% by weight over the combined weight of compounds (I) and (II) in the blend of a compound (II) which is a polyethylenically unsaturated monomer selected from the group consisting of a $C_2$-$C_{24}$ alkyl di- or polyester of (meth)acrylic acid, a $C_2$-$C_{24}$ alkyl di- or polyamide of (meth)acrylic acid and mixtures thereof, and which:
   A1. contains two or more (meth)acrylate ester groups or two or more (meth)acrylate amide groups per monomer, and
   B1. has a molecular weight which, once divided by the number of (meth)acrylate ester or amide groups, gives a value of more than 85 and lower than 135.
4. The microcapsule according to any one of points 1 to 3, wherein the polymeric shell further comprises solid colloidal particles having an average primary particle size comprised between 5 nm and 1 µm.
5. The microcapsule according to any one of points 1 to 4, wherein the neutral monomethacrylate monomer (Ia) is selected from 2-hydroxyethyl methacrylate, 2-hydroxypropyl methacrylate, 3-hydroxypropyl methacrylate, glycidyl methacrylate, triethylene glycol methyl ether methacrylate; PEG300 methacrylate methyl ether, and mixtures thereof.
6. The microcapsule according to any one of points 1 to 5, wherein the neutral monomethacrylate monomer (Ia) includes 2-hydroxyethyl methacrylate.
7. The microcapsule according to any one of points 1 to 6, wherein the another neutral monoethylenically unsaturated monomer (Ib) includes methyl methacrylate and/or ethyl methacrylate.
8. The microcapsule according to any one of points 1 to 7, wherein the compound (II) is a $C_2$-$C_{24}$ alkyl di- or polyester of (meth)acrylic acid.
9. The microcapsule according to point 8, wherein the compound (II) includes one or more of 1,4-butane diol dimethacrylate, ethylene glycol dimethacrylate and 1,3-propylene glycol dimethacrylate.
10. The microcapsule according to any one of points 1 to 9, wherein:
   the neutral monomethacrylate monomer (Ia) comprises 2-hydroxyethyl methacrylate;
   the another neutral monoethylenically unsaturated monomer (Ib) is a $C_1$-$C_{24}$ linear or branched alkyl ester of methacrylic acid and comprises methyl methacrylate and/or ethyl methacrylate;
   the compound (II) which is a $C_2$-$C_{24}$ alkyl di- or polyester of methacrylic acid and comprises one or more of 1,4-butane diol dimethacrylate, ethylene glycol dimethacrylate and 1,3-propylene glycol dimethacrylate.
11. The microcapsule according to any one of points 1 to 10, wherein the blend is substantially free of any one of (meth)acrylic acid, $C_1$-$C_{24}$ alkyl monoesters of acrylic acid and $C_2$-$C_{24}$ alkyl polyesters of acrylic acid.
12. The microcapsule according to any one of points 1 to 11, wherein the combined amounts of compounds (I) and (II) make 100% of the weight of the blend.
13. A water-based dispersion including the microcapsule as defined in any one of points 1 to 12.
14. A process for the manufacture of the microcapsule as defined in any one of points 1 to 12, which is a free radical polymerization process and which includes the following steps:
   a) providing an oil-in-water emulsion having an oil phase and a water phase, said oil-in-water emulsion being obtainable by mixing:
      a polymerization initiator,
      a perfume composition including a fragrance,
      an emulsifier, and
      the blend as defined in any one of points 1 to 12,
   b) triggering polymerization within the oil-in-water emulsion obtained in step a),
   c) letting the polymerization propagate thereby obtaining microcapsules.
15. A product comprising the microcapsule as defined in any one of points 1 to 12 or the water-based dispersion as defined in point 13, and which is a non-edible consumer goods product, a household cleaner or laundry product, a personal care product or a cosmetic product.

Advantageous Effects of Invention

The microcapsule containing one or more fragrances is suitable for inclusion in non-edible consumer goods products, laundry products, personal care products and cosmetic products. The microcapsule can be obtained in an economic and efficient manner by polymerizing an emulsion so that emulsion droplets are encapsulated into a subsequently cured polymeric shell.

DESCRIPTION OF EMBODIMENTS

Unless otherwise stated, all percentages are weight percentages.

Unless otherwise indicated "an" or "a" means one or more.

Unless otherwise indicated, all chemical terms have the meanings defined by the IUPAC Compendium of Chemical Terminology $2^{nd}$ Edition Compiled by A D McNaught and A Wilkinson Blackwell Scientific Publications Oxford 1997 and IUPAC Nomenclature of Organic Chemistry, published by Blackwell Scientific Publications Oxford 1993 ISBN 0632034882.

Unless otherwise indicated, the language "blend", "a blend" or "monomer blend" refers to the blend including compounds (I) and (II).

Unless otherwise indicated, compounds referred to as monomer(s) are monomers which can be polymerized by free radical polymerization.

Unless otherwise indicated "(meth)acrylate" (or "(meth) acrylic") means methacrylate (or methacrylic) and/or acrylate (or acrylic). For example, it means methacrylate (or methacrylic). For example it means acrylate (or acrylic). For example it means methacrylate (or methacrylic) and acrylate (or acrylic).

Unless otherwise indicated, methacrylate and acrylate ester groups are groups having molecular weight of 85 and 71 mass units, respectively, and the following structures

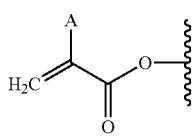

wherein A is $CH_3$ for a methacrylate ester group or A is H for an acrylate ester group.

Unless otherwise indicated, methacrylate or acrylate amide groups are groups having molecular weight of 84 and 70 mass units, respectively, and the following structures

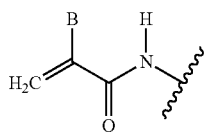

wherein B is $CH_3$ for a methacrylate amide group or B is H for an acrylate amide group.

Unless otherwise indicated, room temperature is 20° C.

Certain substances, notably perfumery molecules, may exist as distinct isomers (or as mixture of distinct isomers). Hereinafter, they may be identified also by means of their CAS number. In these cases, the CAS number of a single isomer is reported. However, and unless otherwise indicated, the reference shall be understood to cover all existing isomers.

The present disclosure discloses a microcapsule which comprises, such as consists of, a perfume composition enclosed within a polymeric shell.

Methods of preparation of perfume-containing microcapsules are described for example in MICROENCAPSULATION: Methods and Industrial Applications Edited by Benita and Simon (Marcel Dekker, Inc. 1996) and in Kirk Othmer Encyclopedia of Chemical Technology Microencapsulation by C. Thies. Microcapsules obtainable by free radical polymerization are well known to those working in the field of e.g. encapsulated perfumes and are structurally (and dimensionally) different from other types of capsules such as conventional seamless soft capsules or two-piece hard capsules used e.g. in pharmacy to orally or rectally administrate substances to a subject.

The microcapsules presently disclosed are not intended for oral or rectal administration to human or animal subjects.

A microcapsule as presently disclosed may have a shell thickness comprised between about 100 nm and 800 nm, such as between about 200 nm and 700 nm, for example between about 300 nm and 600 nm.

A microcapsule as presently disclosed may have a perfume composition-to-shell weight ratio which is comprised between 50:1 and 1:1, such as between 30:1 and 1:1, or between 20:1 and 1:1, for example between 10:1 and 1:1.

The microcapsule presently disclosed may be substantially spherical.

The microcapsule presently disclosed may have an average particle size (median volume particle size D(v; 0.5) value) equal to or greater than 7.5 microns (7.5 µm), for example equal to or greater than 10 µm, such as equal to or greater than 15 µm, or equal to or greater than 20 µm, for example equal to or greater than 25 µm. The microcapsule presently disclosed may have an average particle size equal to or less than 60 microns (60 µm), for example equal to or less than 50 µm, such as equal to or less than 45 µm, for example equal to or less than 40 µm. The microcapsule presently disclosed may have an average particle size comprised between 7.5 microns (7.5 µm) and 60 microns (60 µm), or between 7.5 µm and 50 µm, or between 10 µm and 50 µm, or between 7.5 µm and 45 µm, or between 10 µm and 45 µm, or between 15 µm and 45 µm, or between 15 µm and 40 µm, or between 20 µm and 45 µm, or between 25 µm and 45 µm, or between 25 µm and 40 µm, or between 25 µm and 35 µm.

Microcapsules obtainable by free-radical polymerization have typically quite small (e.g. less than about 7 microns) average particle sizes. This might be due to a technical belief that this size better copes with an efficient polymerization, thus leading to capsules with better properties. At the same time, it was also believed that average particle size did not have a significant impact on final capsule leakage. The experimental results obtained by the present Applicant showed however that no significant issues with polymerization are met when targeting larger sizes and that larger average particle sizes may bring about an advantage in terms of leakage. If microcapsules with dimensions which do not make them visible at naked eye when deposited on a black surface are desired, then it is recommendable to target an average particle size of less than e.g. 70 microns.

The preferred technique used in the present disclosure to measure the microcapsule average particle size is light scattering using for example a Horiba® or a Malvern® Laser scattering particle Size Distribution analyzer or an equivalent instrument working on the principle of low angle laser light scattering (LALLS) following the general guidelines set out in ISO 13320 "Particle Size Analysis—Laser Diffraction Methods".

In one embodiment, the polymeric shell further comprises solid colloidal particles (also known as particulate colloids) having an average primary particle size comprised between 5 nm (nanometer) and 1 µm (micrometer) as measured for example through dynamic light scattering. Free radical polymerization for microcapsule preparation generally includes the initial formation of an oil-in-water emulsion. Particulate colloids allow obtaining Pickering oil-in-water emulsions stabilized by limited coalescence. The process of formation of Pickering emulsions is known. It is discussed for example in Whitesides and Ross, J. Interface Colloid Sci. 196, 48-59(1995).

Examples of materials which can be suitably used in the form of solid colloidal particles in the microcapsules presently disclosed are silica, quartz, glass, aluminum (AlO(OH)), alumino-silicates (e.g. clays), silicon, copper, tin (SnO), talc, inorganic oxides or hydroxides (e.g. $Fe_2O_3$, $TiO_2$, $Cr_2O_3$), steel, iron, asbestos, nickel, zinc, lead, marble, chalk ($CaCO_3$), gypsum ($CaSO_4$), barytes (e.g. $BaSO_4$), graphite and carbon black. Preferred materials are silica, alumino-silicates and inorganic oxides or hydroxides. Silica is a highly preferred material.

Solid colloidal particles suitable for the present disclosure may or may not be surface modified. Surface modification may either impart the ability to materials to partition to the interface of water and oil phases or it may improve the compatibility between the materials and the microcapsule polymeric shell. Examples of surface modification include chemical treatments to increase or decrease particles hydrophobicity. Alternatively, surface modifying agents can be adsorbed onto particles surface to impart appropriate surface active properties. Alternatively, particles may be modified by means of coupling agents which improve the compatibility between the materials and the microcapsule polymeric shell. Techniques to modify particle surfaces are discussed for example in "Nanoparticle Technology handbook" 1st edition, year 2007, Application 41 (pages 593-596) "Surface modification of inorganic nanoparticles by organic functional groups". Modified (as well as non-modified) solid colloidal particles are commercially available.

Examples of suitable colloidal silicas may be dry fumed silicas (such as commercially available in the Aerosil® range from Evonik®) or aqueous colloidal silica dispersions (such as those commercially available in the Ludox® range from Du Pont®). Dry silica particles may be fumed silica particles or condensed silica particles. Fumed silicas are particularly adapted for stabilizing emulsions with droplet sizes in the range of 10 μm to 100 μm. For larger droplets, colloidal silicas might be more appropriate. Suitable grades of fumed silica are Aerosil® 200 (a hydrophilic fumed silica with a specific surface area of 200 m²/g) and Aerosil® R816 having a BET surface area of 190±20 m²/g and an average primary particle size of about 12 nm, both available from Evonik®.

Amounts of solid colloidal particles may be comprised between 0.025% and 10%, such as between 0.05% and 7.5%, for example between 0.1% and 5%, such as between 0.2% and 3%, or between 0.3% and 2%, or between 0.3% and 1.2%, such as 0.6% by weight over the weight of a dried slurry.

Compound (I) is a Combination of:
ia) between 50% and 100%, such as between 60% and 100%, for example between 70% and 100% by weight over the weight of the combination of a neutral monomethacrylate monomer (Ia) having a solubility in water at 20° C. equal to, or more than 2 g/100 ml,
ib) between 0% and 50%, such as between 0% and 40%, for example between 0% and 30% by weight over the weight of the combination of another neutral monoethylenically unsaturated monomer (Ib), and
ic) between 0% and 15%, such as between 0% and 5% by weight over the weight of the combination of a ionized or ionizable monoethylenically unsaturated monomer (Ic).

Adopting the above combination allows to obtain microcapsules which display shell properties which are pH-independent in a pH range commonly met in liquid household, laundry personal care and cosmetic products, such as fabric conditioners and antiperspirants (acidic pH) or liquid laundry detergents and hard surface cleaners (alkaline pH). For example, this pH range is comprised between 2 and 12, such as more than 4, for example between 4 and 12.

In the present description and unless otherwise indicated, "neutral" means that the monomethacrylate monomer is non-ionized or ionized in an amount of less than 20 mol % when measured in deionized water at 20° C. at a pH of 2 and 12. For example, a monomethacrylate monomer is neutral if it does not contain functional groups which are permanently ionized such as quaternized amines, for example quaternary alkyl ammonium salts. For example, a neutral monomethacrylate monomer may contain functional groups whose protonated species have $pK_a$ greater than about 12.5, such as greater than about 12.7, for example greater than about 13, such as comprised between about 13 and 30. For example, a monomethacrylate monomer is neutral if it does not contain functional groups such as carboxylic acid groups, primary or secondary amine groups. Alternatively, a neutral monomethacrylate monomer may contain functional groups such as primary alcohols, primary or secondary amides or ether groups.

Monomer (Ia) has a solubility in water at pH 7 and 20° C. equal to, or more than 2 g/100 ml, for example more than 3 g/100 ml, such as more than 4 g/100 ml or more than 5 g/100 ml. Monomer (Ia) is a hydrophilic one. Water solubility is conveniently measured according to OECD method 105—water solubility adopted on 27 Jul. 1995 (OECD GUIDELINE FOR THE TESTING OF CHEMICALS).

Monomer (Ia) may be selected from 2-hydroxyethyl methacrylate, hydroxypropyl methacrylate, methacrylamide, glycidyl methacrylate, methacrylonitrile, poly(ethylene glycol) methyl ether methacrylate, for example PEG300 methacrylate methyl ether or for example a poly(ethylene glycol) methyl ether methacrylate wherein the average number of PEG units is comprised between 3 and 20, for example between 5 and 10 (e.g. triethylene glycol methyl ether methacrylate; tetraethyleneglycol methyl ether methacrylate; penta ethyleneglycol methyl ether methacrylate; decaethyleneglycol methyl ether methacrylate; pentadecaethyleneglycol methyl ether methacrylate), and mixtures thereof. For example, monomer (Ia) may be selected from 2-hydroxyethyl methacrylate, 2-hydroxypropyl methacrylate, 3-hydroxypropyl methacrylate, glycidyl methacrylate, triethylene glycol methyl ether methacrylate; PEG300 methacrylate methyl ether, and mixtures thereof. For example, monomer (Ia) may be selected from 2-hydroxyethyl methacrylate, glycidyl methacrylate, poly(ethylene glycol) methyl ether methacrylate and mixtures thereof.

Preferably, monomer (Ia) includes at least 2-hydroxyethyl methacrylate. For example, 2-hydroxyethyl methacrylate may represent at least 10% or at least 20% or at least 30% or at least 40% or at least 50% or at least 60% or at least 70% or at least 80% or at least 90% by weight of the monomer (Ia) in the blend. Monomer (Ia) may consist of 2-hydroxyethyl methacrylate.

Monomer (Ib) is a neutral monoethylenically unsaturated monomer other than, i.e. different from monomer (Ia). Neutral is defined as discussed above.

Suitable examples of monomers (Ib) may be:
optionally substituted $C_1$-$C_{24}$ linear or branched alkyl esters of $C_3$-$C_6$ monoethylenically unsaturated mono- or poly carboxylic acids,
and
optionally substituted $C_3$-$C_6$ cycloalkyl esters of $C_3$-$C_6$ monoethylenically unsaturated mono- or poly carboxylic acids.

Optional substituents may be —OH, —OR, —C(O)R, wherein R is $C_1$-$C_4$ alkyl while a preferred mono- or poly carboxylic acid is methacrylic acid.

Monomer (Ib) may conveniently have a solubility in water at pH 7 and 20° C. of less than 2 g/100 ml. It may be totally insoluble in water. Monomer (Ib) is a hydrophobic one. Water solubility is conveniently measured according to OECD method 105—water solubility adopted on 27 Jul. 1995 (OECD GUIDELINE FOR THE TESTING OF CHEMICALS).

Monomer (Ib) may be selected from methyl methacrylate, ethyl methacrylate, n-propyl methacrylate, isopropyl methacrylate, tert-butyl methacrylate, isobutyl methacrylate, n-butyl methacrylate, benzyl methacrylate, isobornyl methacrylate, cyclohexyl methacrylate, tetrahydrofurfuryl methacrylate, mono(ethylene glycol) methyl ether methacrylate, di(ethylene glycol) methyl ether methacrylate, and mixtures thereof. For example, monomer (Ib) may be selected from methyl methacrylate and/or ethyl methacrylate.

Preferably, monomer (Ib) includes at least methyl methacrylate. Preferably, monomer (Ib) includes at least ethyl methacrylate. For example, methyl methacrylate and/or ethyl methacrylate may be present in an amount of at least 10%, such as at least 20%, for example at least 30%, such as at least 40%, or at least 50%, or at least 60%, or at least 70%, such as at least 80%, for example at least 90% by weight over the combined weight of all monomers (Ib) present in the blend. Monomer (Ib) may consist of methyl methacrylate and/or ethyl methacrylate.

Monomer (Ic) is a ionized or ionizable monoethylenically unsaturated monomer.

In the present description and unless otherwise indicated, "ionized or ionizable" means that monomer (Ic) is either permanently ionized or ionized in an amount of more than 20 mol % when measured in deionized water at 20° C. at a pH of either 2 or 12. For example, monomer (Ic) is ionized or ionizable if it contains functional groups which are permanently ionized such as quaternized amines, for example quaternary alkyl ammonium salts. For example, monomer (Ic) may contain functional groups whose protonated species have $pK_a$ lower than about 12.5, such as lower than about 11, for example lower than about 10, such as comprised between about 10 and 0. For example, an ionized or ionizable monomer (Ic) may contain one or more of functional groups such as carboxylic acid groups, sulfonic acid groups and primary or secondary amine groups.

Examples of monomer (Ic) are (meth)acrylic acid, 3-(methacryloylamino)propyl]trimethylammonium chloride (MAPTAC), dimethyldiallyl ammonium chloride, maleic acid, itaconic acid, 2-(diethylamino)ethyl methacrylate, dimethylaminoethyl methacrylate, 2-(tert-Butylamino)ethyl methacrylate, N-[3-(dimethylamino)propyl]methacrylamide, acryloxyethyltrimethyl ammonium chloride, 2-ethyl(2-oxoimidazolidin-1-yl)methacrylate and mixtures thereof. Preferred examples are methacrylic acid and/or 3-(methacryloylamino)propyl]trimethylammonium chloride.

Compound (II) is a polyethylenically unsaturated monomer. Compound (II) may also be referred to as crosslinker due its crosslinking function in the manufacturing of the capsule shell.

Compound (II) may be a di- or poly(meth)acrylate monomer meaning that it contains two or more (meth)acrylate ester or amide groups.

Examples of $C_2$-$C_{24}$ alkyl di- or polyamide of (meth) acrylic acid are N,N-methylenebis(2-methyl(meth)acrylamide), N,N-ethylenebis(2-methyl(meth)acrylamide) and the amides obtainable by reacting melamine with (meth)acrylic acid.

Preferably, compound (II) is selected from the group consisting of divinylbenzene, trivinylbenzene, a $C_2$-$C_{24}$ alkyl di- or polyester of methacrylic acid, a $C_2$-$C_{24}$ alkyl di- or polyamide of methacrylic acid and mixtures thereof, such as a $C_2$-$C_{24}$ alkyl di- or polyester of methacrylic acid, a $C_2$-$C_{24}$ alkyl di- or polyamide of methacrylic acid and mixtures thereof, for example a $C_2$-$C_{24}$ alkyl di- or polyester of methacrylic acid.

Suitable di- or polyesters are those resulting from the esterification of methacrylic acid with linear or branched polyhydric $C_2$-$C_{24}$, such as $C_2$-$C_{12}$, alcohols or $C_2$-$C_{24}$, such as $C_2$-$C_{12}$, polyethylene glycols. Suitable polyhydric alcohols may be those having a number average molecular weight of up to about 6000. Suitable polyethylene glycols may be those having a number average molecular weight of up to about 7500. Polyhydric alcohols are advantageously diols. Polyethylene glycols are advantageously di-, tri- or tetra-ethylene glycols.

Examples of compound (II) are 1,4-butane diol dimethacrylate (molecular weight MW about 226); 1,3-butylene glycol dimethacrylate (MW about 226); pentaerythritol trimethacrylate (MW about 340); glycerol trimethacrylate (MW about 296); 1,2-propylene glycol dimethacrylate (MW about 212), 1,3-propylene glycol dimethacrylate (MW about 212), ethylene glycol dimethacrylate (MW about 198), diethylene glycol dimethacrylate (MW about 242); glycerol dimethacrylate (MW about 228); 1,6-hexane diol dimethacrylate (MW about 226), trimethylolpropane trimethacrylate (MW about 338); ethoxylated pentaerythritol tetramethacrylate (MW about 585), divinylbenzene, trivinylbenzene and mixtures thereof. Preferred examples are 1,4-butane diol dimethacrylate, 1,3-propylene glycol dimethacrylate, ethylene glycol dimethacrylate, diethylene glycol dimethacrylate and mixtures thereof, such as 1,4-butane diol dimethacrylate, ethylene glycol dimethacrylate, 1,3-propylene glycol dimethacrylate and mixtures thereof.

Compound (II) may include at least 1,4-butane diol dimethacrylate, 1,3-propylene glycol dimethacrylate, ethylene glycol dimethacrylate or diethylene glycol dimethacrylate, such as at least 1,4-butane diol dimethacrylate and/or ethylene glycol dimethacrylate and/or 1,3-propylene glycol dimethacrylate. For example, compound (II) may include at least, or consist of, 1,4-butane diol dimethacrylate. For example, compound (II) may include at least, or consist of, ethylene glycol dimethacrylate. For example, compound (II) may include at least, or consist of, 1,3-propylene glycol dimethacrylate. For example, compound (II) may include the above crosslinkers in an amount of at least 10%, such as at least 20%, for example at least 30%, such as at least 40%, or at least 50%, or at least 60%, or at least 70%, such as at least 80%, for example at least 90% by weight over the combined weight of compound (II) in the blend.

In one aspect, compound (II) may be a $C_2$-$C_{24}$ alkyl di- or polyester of (meth)acrylic acid, preferably methacrylic acid, and:

A1. it contains two or more, for example 2 to 6, or 2 to 4 such as 2 or 3 or 4 (meth)acrylate ester or amide groups per monomer, and B1. it has a MW (molecular weight, expressed as mass units) which, once divided by the number of (meth)acrylate ester or amide groups, gives a value of more than about 85, for example more than about 90, and lower than about 135, such as lower than about 121.

In one embodiment, compound (II) meets conditions A1 and B1 above provided that any one or more of 1,4-butane diol dimethacrylate, ethylene glycol dimethacrylate, 1,3-propylene glycol dimethacrylate, ethylene glycol dimethacrylate and diethylene glycol dimethacrylate are excluded.

In one aspect, compound (II) may be a polyethylenically unsaturated monomer as defined above such that the microcapsule provides for a fragrance leakage of less than about 60%, such as less than about 45%, for example less than about 35%, when tested upon storage for 4 weeks at 40° C. in a test liquid base, according to a leakage test method, when the microcapsule is prepared according to a leakage test manufacturing procedure, and the microcapsule encapsulates fragrance no. 1, the test liquid base, the leakage test method, the manufacturing procedure and the fragrance no. 1 being as defined in the examples presently enclosed.

In one embodiment, compound (II) meets the above leakage condition provided that any one or more of 1,4-butane diol dimethacrylate, ethylene glycol dimethacrylate, 1,3-propylene glycol dimethacrylate, ethylene glycol dimethacrylate and diethylene glycol dimethacrylate are excluded.

Compound (II) may be present between 30 and 60%, or between 40 and 55% by weight over the combined weight of compounds (I) to (II).

As experimentally shown in the enclosed examples, the choice of the crosslinker may have an effect e.g. in terms of resistance of the capsule shell.

The shell may comprise in polymerized form a blend including, preferably consisting of:
i) between 40% and 70%, preferably between 40% and 60% by weight over the combined weight of compounds (I) to (II) in the blend of a compound (I) which is a combination of:
  ia) between 70% and 100% by weight over the weight of the combination of 2-hydroxyethyl methacrylate;
  ib) between 0% and 30% by weight over the weight of the combination of a $C_1$-$C_{24}$ linear or branched alkyl ester of methacrylic acid such as methyl and/or ethyl methacrylate;
  ic) between 0% and 5% by weight over the weight of the combination of methacrylic acid and/or 3-(methacryloylamino)propyl]trimethylammonium chloride; and
ii) between 30% and 60% by weight over the combined weight of compounds (I) to (II) in the blend of a compound (II) which is selected from a $C_2$-$C_{24}$ alkyl di- or polyester of methacrylic acid, a $C_2$-$C_{24}$ alkyl di- or polyamide of methacrylic acid and mixtures thereof, such as a monomer selected from 1,4-butane diol dimethacrylate, ethylene glycol dimethacrylate, 1,3-propylene glycol dimethacrylate and mixtures thereof.

The blend may consist of compounds (I) and (II) as presently defined, meaning that the combined amounts of compounds (I) to (II) make 100% of the weight of the blend.

The blend may be substantially free of monoethylenically unsaturated monomers other than compound (I) as presently defined. The blend may be substantially free of polyethylenically unsaturated monomers other than compound (II) as presently defined.

The blend may be substantially free of one or more of:
monomers, such as acrylic acid, which contain carboxylic acid (—COOH) groups and/or primary or secondary amine groups, in either neutral or ionized form;
$C_1$-$C_{24}$ alkyl monoesters of acrylic acid;
$C_2$-$C_{24}$ alkyl poly (e.g. di-, tri-, tetra- or penta) esters of acrylic acid;
monomers containing a carboxyl anhydride group (e.g. a monomer containing symmetric or asymmetric intermolecular anhydrides of monoethylenically unsaturated monocarboxylic acids having 3 to 20 carbon atoms);
monomers containing alkylenebis(meth)acrylamide group (e.g. N,N'-unsubstituted $C_{1-18}$ alkylene bis(meth) acrylamides or linear or cyclic N,N'-substituted $C_{1-18}$ alkylene bis(meth)acrylamides wherein substituents are selected from $C_{1-8}$ alkyl, $C_{1-8}$ hydroxyalkyl or polyoxy($C_{1-4}$)alkylene of 2 to 500 alkylene units or the alkyl substituents together with the nitrogen atoms to which they are attached form a 5- to 8-membered ring).

The blend is preferably substantially free of $C_1$-$C_{24}$ alkyl monoesters of acrylic acid and/or $C_2$-$C_{24}$ alkyl polyesters of acrylic acid. For example, it is preferred that the blend be substantially free of acrylic acid, $C_1$-$C_{24}$ alkyl monoesters of acrylic acid, $C_2$-$C_{24}$ alkyl polyesters of acrylic acid and $C_2$-$C_{24}$ alkyl polyamides of (meth)acrylic acid. For example, the blend may be substantially free of acrylic and/or methacrylic acid, $C_1$-$C_{24}$ alkyl monoesters of acrylic acid, $C_2$-$C_{24}$ alkyl polyesters of acrylic acid and $C_2$-$C_{24}$ alkyl polyamides of (meth)acrylic acid.

In the present disclosure, and unless otherwise indicated, substantially free mean less than 5% such as less than 1%, for example 0% by weight over the weight of the blend.

The perfume composition includes a fragrance, i.e. an olfactively active (i.e. odoriferous) material typically but not necessarily providing a pleasant smell.

The perfume composition may represent at least 50%, such as at least 60% by weight of the weight of dried slurry. The perfume composition may represent up to 90%, such as up to 80% by weight of the weight of dried slurry. Unless otherwise indicated, dried slurry means the product obtainable by subjecting a microcapsule slurry as defined below to the solid content measurement method as discussed in the examples.

The perfume composition presently disclosed may include, such as consist of, a fragrance or it may also include a perfumery acceptable solvent and/or a benefit agent. For example, the fragrance may represent at least 40%, such as at least 60%, for example at least 80%, such as at least 90% by weight over the weight of the perfume composition. The balance of the perfume composition may be represented by perfumery acceptable solvents and/or benefit agents as defined below.

The fragrance may consist of a single, typically organic, molecule or a mixture of distinct molecules. Hereinafter, these molecules will also be referred to as "perfumery molecules". Fragrance typically used in the field of perfumery and suitable for the purposes of the present disclosure are described more fully in S. Arctander, Perfume Flavors and Chemicals 1969, Vols. I and II, Montclair, N.J. and in Allured's Flavor and Fragrance Materials 2007 ISBN 978-1-93263326-9 published by Allured Publishing Corp. The term fragrance comprises both naturally occurring as well as synthetic fragrances known for use in perfumes. Perfumery molecules advantageously display balanced volatility/hydrophobicity so as to be olfactively noticeable when the microcapsules release them but also sufficiently water-insoluble to be emulsified during encapsulation.

The perfume composition may comprise at least two, such as at least four, or at least eight distinct fragrances. For example a fragrance may comprise at least two distinct perfumery molecules whose combination does not display a solid-liquid phase transition at a temperature comprised between −20° C. and 120° C.

A fragrance may comprise one or more distinct perfumery molecules each having a molecular weight greater than 100, preferably greater than 125 and lower than 325, preferably lower than 300, more preferably lower than 275. A fragrance may comprise one or more distinct perfumery molecules each having a boiling point comprised between about 80° C. and 400° C., such as between about 100° C. and 350° C. when measured at 760 mm Hg. It is preferable that perfumery molecules have water solubility below 1.5 g/100 ml at 20° C. It is possible for example that a fragrance according to the present disclosure contains at least 80% by weight over the weight of the fragrance of a perfumery molecule as defined above. For example, at least 90% by weight over the weight of all perfumery molecules present in the fragrance may be represented by one or more perfumery molecules having water solubility at 20° C. comprised between 0.0005 g/100 ml, such as 0.002 g/100 ml, and 1 g/100 ml.

EP1894603A1, published on Mar. 5, 2008 and having title "Encapsulation of bulky fragrance molecules", discloses certain perfumery molecules which are therein referred to as "bulky". Bulky perfumery molecules typically leak less than non-bulky perfumer molecules. Examples of bulky molecules are diphenyl oxide (101-84-8), benzyl salicylate (118-58-1), cyclohexyl salicylate (25485-88-5), phenyl ethyl phenylacetate (102-20-5), Lyrame (67634-12-2), Orriniff (125352-06-9), Santalex T (68877-29-2), Karanal (117933-89-8), vanillin propylene glycol acetal (68527-74-2), Indolene 50 (68908-82-7), Okoumal (131812-67-4), cyclohexyl anthranilate (7779-16-0), 2-cyclohexylidene-2-phenyl acetonitrile (10461-98-0), cyclohexyl cinnamate (7791-17-1), benzyl cinnamate (103-41-3), benzyl eugenol (120-11-6), cinnamyl anthranilate (87-29-6), cinnamyl cinnamate (122-69-0), cinnamyl phenyl acetate (7492-65-1), Doremox (24720-09-0), dibenzyl ketone (102-04-5), and benzophenone (119-61-9); 1,5-dioxaspiro(5.5)undecane 2-methyl (6413-26-9), 2,2,3',7',7'-pentamethylspiro(1,3dioxan-5,2'-norcarane) (12151-67-0 and 12151-68-1), Vigoflor (68480-11-5), 3,3-dimethyl-1,5-dioxaspiro(5,5)undecane (707-29-9), Oxaspirane (68228-06-8), and 8-methyl-1-oxaspiro(4,5)decan-2-one (94201-19-1); yara yara (93-04-9), coumarin (91-64-5), methyl naphthyl ketone, (941-98-0) isobutylquinoline (65442-31-1), Galaxolide (01222-05-5), Tonalide (021145-77-7), Cashmeran (033704-61-9), Cyclacet (5413-60-5), Cyclaprop (17511-60-3), Cyclabute (067634-20-2), Cedramber (019870-74-7), Dulcinyl (55418-52-5), Grisalva (68611-23-4), Ambrinol 20T (41199-19-3), beta caryophyllene, caryophyllene, caryophyllene acetate, alpha cedrene, 8-cedren-13-ol, cedrol, cedryl acetate, cedrenyl acetate, cedryl formate, cedryl methyl ether, Heliobouquet (1205-17-0), Fruitate (080657-64-3), 1,4-cineole (470-67-7), 1,8-cineole (470-82-6), borneol (464-45-9), bornyl acetate (76-49-3), isoborneol (124-76-5), isobornyl acetate (125-12-2), isobornyl formate (1200-67-5), isobornyl methyl ether (5331-32-8), isobornyl propionate (2756-56-1), Neoproxen (122795-41-9), Isoproxen (90530-04-4), Florosantol, Cedanol (7070-15-7), fenchyl alcohol (1632-73-1), ambrox (6790-58-5), iso E super (54464-57-2), Patchoulol (5986-55-0), norpatchoulenol (41429-52-1), Isolongifolanone (23787-90-8), amboryl acetate (59056-62-1), Nootkatone (4674-50-4), Florex (69486-14-2), Cedryl methyl ether (19870-74-7 and 67874-81-1), alpha pinene (80-56-8), beta pinene (127-91-3), dihydroactinidiolide (1536-74-8), alpha copaene (3856-25-5), cam phene (79-92-5), camphor (464-49-3), Phantolide (15323-35-0), Celestolide (13171-00-1), Traseolide (68140-48-7), β naphthyl isobutyl ether (2173-57-1), decahydro-β-naphthyl acetate (10519-11-6), Scentenal (86803-90-9), Plicatone (41724-19-0), Rhubofix (41816-03-9), and Cetalox (3738-00-9), para tertiarybutyl cyclohexanol (98-52-2), para tertiary butyl cyclohexyl acetate (32210-23-4), ortho teriary butyl cyclohexanol (13491-79-7), ortho tertiary butyl cyclohexyl acetate (88-41-5), para tertiary butyl cyclohexanone, Hedione (24851-98-7), α ionone (127-41-3), β ionone (14901-07-6), γ ionone (79-76-5), α damascone (24720-09-0), β damascone (23726-92-3), δ damascone (57378-68-4), γ damascone (35087-49-1), β damascenone (23696-85-7), Bacdanol (28219-61-6), Clarycet (131766-73-9), Coniferan (67874-72-0), Dihydrofloralol (68480-15-9), Ebanol (67801-20-1), Fraistone (6290-17-1), Isocyclogeraniol (68527-77-5), Jasmelia (58285-49-3), fenchol (22627-95-8), fenchyl acetate (13851-11-1), Levosandol (28219-61-6), methyl dioxolan (6413-10-1), Nopol (128-50-7), Nopyl acetate (35836-72-7), 2,6,6-trimethyl-1-cyclohexen-1-acetaldehyde (472-66-2), 2,4,6-trimethyl-3-cyclohexene-1-carboxaldehyde (1335-66-6), 2,4,6-trimethyl-3-cyclohexene-1-methanol (68527-77-5), 3-methyl-5-propyl-2-cyclohexen-1-one (3720-16-9), Dynascone (56973-85-4), alpha iso methyl ionone (1335-46-9) Polysantol (107898-54-4), Romascone (81752-87-6), Timberol (70788-30-6), Amber Core (139504-68-0), Precyclemone B (52474-60-9), Boronal (3155-71-3), 2,2,5-trimethyl-5-pentylcyclopentanone (65443-14-3), Brahmanol (72089-08-8), Sandalmysore core (28219-60-5), Sandalore (65113-99-7), 4-tert-pentylcyclohexanone (16587-71-6), Kephalis (36306-87-3), Floramat (67801-64-3), Jasmapol (37172-53-5), 3-oxo-2-(2-cis pentenyl) cyclopentane acetic acid methyl ester (1211-29-6), and 2-pentyl-3-methyl-2cyclopenten-1-one (1128-08-1); Ethylene Brassylate (105-95-3), 3-methylcyclopentadecanone (541-91-3), 3-methylcyclopentadecenone (82356-51-2), 3-methylcyclopentadecanol (4727-17-7), Exaltolide (106-02-5), Exaltone (502-72-7), Exaltenone (14595-54-1), Cedroxyde (71735-79-0), 15-pentadecenolide (34902-57-3), (z)-9-cycloheptadecen-1-one (542-46-1), 12-methy-14-tetradec-9-enolide, am brettolide (28645-51-4), Ambretone (37609-25-9), Violiff (87731-18-8), Trimofix O (28371-99-5), cyclodecyl methyl ether (2986-54-1), and ethoxymethoxycyclododecane (5867-11-6); lilial (80-54-6), Acetoketal (5406-58-6), 4-t-butylbenzenepropionaldehyde (18127-01-0), dimethylbenzylcarbinyl acetate (151-05-3) and Damascol 4 (4927-36-0); 1,3,5-Trimethoxybenzene (621-23-8), acetyl Eugenol (93-28-7), acetyl vanillin (881-68-5), anisyl acetate (104-21-2), methyl eugenol (93-15-5), Musk thibetene (145-39-1), Musk ambrette (83-66-9), 3,4-dimethoxybenzoic acid (93-07-2), 3,4 methylenedioxybenzyl acetate (326-61-4) and veratraldehyde (120-14-9).

Accordingly, the present disclosure discloses a microcapsule as defined above wherein the perfume composition includes a fragrance and that fragrance includes a bulky perfumery molecule. A fragrance may include a bulky perfumery molecule in amount greater than 20%, such as greater than 40%, for example greater than 60%, or greater than 80% by weight over the weight of the fragrance. In case the perfumery composition contains more than one fragrance, each fragrance may independently have the above content of bulky perfumery molecules.

It is convenient that fragrances for incorporation in a perfume composition as presently disclosed be selected so that the perfume composition contains less than 25%, such as less than 15%, for example less than 5% by weight of a perfumery molecule selected from the group consisting of limonene (CAS: 5989-27-5), carvone (CAS: 99-49-0, 2244-16-8), ethyl safranate (CAS: 35044-57-6), myrcene (CAS: 123-35-3), myrcenol (CAS: 543-39-5), myrcenyl acetate (CAS: 1118-39-4), eugenol (CAS: 97-53-0), eugenyl acetate (CAS: 93-28-7), chavicol (CAs: 501-92-8), estragol (CAS: 140-67-0), anethol (CAS: 104-46-1), and mixtures thereof.

The perfume composition may also include a perfumery acceptable solvent. Solvents are conventionally used in the fragrance industry to dilute olf actively powerful ingredients and to facilitate the handling of solid ingredients by dissolving them and handling them as liquids, or simply as a diluent to reduce overall fragrance cost per unit weight. Typically, suitable solvents are water-immiscible solvents, for example solvents having water solubility of less than 10 g/L. Examples of perfumery acceptable solvents are water insoluble hydrocarbon solvents (such as the Isopar® family from ExxonMobil), benzyl benzoate, isopropyl myristate, dialkyl adipates, citrate esters (such as acetyl triethyl citrate and acetyl tributyl citrate) and diethyl phthalate. If present, water miscible solvents (e.g. solvents with water solubility of more than 10 g/100 ml), such as propylene glycol dipropylene glycol, and butylene glycols should preferably be dosed at as low level as possible.

The perfume composition may also include benefit agents. Benefit agents are typically emulsifiable materials having synthetic or natural origin and which can survive storage to deliver a benefit through the use a product containing the microcapsules, such as household, personal care or cosmetic products. Examples of benefit agents are:

agents which suppress or reduce malodour and its perception by adsorbing odour such as zinc ricinoleate, agents improving microcapsule physical-chemical properties such as sucrose octa-acetate or sucrose hexabutyrate di-acetate, gelling agents such as hydroxy fatty acids or the Sylvaclear™ range of materials available from Arizona Chemicals, agents which provide a warming or cooling effect such as cyclohexane carboxamide N-ethyl-5-methyl-2-(1-methylethyl); N 2,3-trimethyl-2-isopropylbutamide; menthyl lactate; (−)-menthoxypropane 1,2-diol, insect repellents such as ethylbutylacetylaminopropionate; N,N-diethyl toluamide; 1-piperidinecarboxylic acid; 2-(2-hydroxyethyl)-1-methylpropyl ester; p-menthane-3,8-diol, antimicrobial agents such as Triclosan™ compound having CAS N° 3380-34-5, or the methyl, ethyl, propyl and butyl para hydroxy benzoate esters, UV absorbers such as octyl methoxycinnamate, butylmethoxydibenzoylmethane, and bis ethylhexyloxyphenolmethoxyphenyltriazine.

Microcapsules may be prepared using a range of known conventional methods such as coacervation, interfacial polymerization, free radical polymerization, or polycondensation. These techniques are well-know, see e.g., U.S. Pat. Nos. 3,516,941, 4,520,142, 4,528,226, 4,681,806, 4,145,184; GB-A-2073132; WO99/17871; and MICROENCAPSULATION Methods and Industrial Applications Edited by Benita and Simon (Marcel Dekker, Inc. 1996).

Advantageously, the microcapsules presently disclosed are manufactured by free radical polymerization (e.g. suspension or emulsion polymerization). Accordingly, the present disclosure discloses a free radical polymerization process for the manufacture of a microcapsule as defined above, which includes the following steps:

a) providing an oil-in-water emulsion having an oil phase and a water phase, said emulsion being obtainable by mixing:
   a polymerization initiator,
   a perfume composition including a fragrance,
   an emulsifier, and
   the monomer blend as defined above,
b) triggering polymerization within the emulsion obtained in step a),
c) letting the polymerization propagate thereby obtaining microcapsules.

Steps a) to c) may be performed in the order in which they are presented.

In one aspect, the present disclosure discloses a microcapsule as instantly defined and which is further obtainable by a free radical polymerization process as defined above.

The microcapsules are conveniently prepared through a polymerization step. The polymerization may be conventional radical polymerization or living radical polymerization. Such radical polymerization processes are known to persons skilled in the art and are further described e.g. in Moad, Graeme; Solomon, David H.; The Chemistry of Radical Polymerization, 2$^{nd}$ ed.; Elsevier, 2006.

A discussion of living radical polymerization, can be found for example in Braunecker, Wade A.; Matyjaszewski, Krzysztof; "Controlled/Living Radical Polymerization: Features, Developments, and Perspectives"; Progress in Polymer Science 2007, Volume 32, Issue 1, Pages 93-146.

The monomers of the blend are as defined above. They are weighed and mixed so as to obtain a monomer blend as defined above. Then, this blend is used in the preparation of the oil-in-water emulsion.

An oil-in-water emulsion (step a)) may be prepared by mixing and dissolving the oil soluble ingredients into a homogeneous solution while separately mixing and dissolving the water soluble ingredients into a homogenous solution. If present, solid colloidal particles are typically admixed to the water solution. An emulsion may be obtained by mixing e.g. with a high shear mixer and for sufficient time the two solutions to create a stable emulsion of a desired particle size. At the same time the emulsion may be purged with nitrogen or other inert gas. Once the air has been removed, polymerization may be heat induced (step b)) by elevating the temperature. The exact temperature and rate of temperature increase is determined by the initiator or combination of initiators to be used. Typically polymerization temperatures are between 40° C. to 90° C. The rate of polymerization can be controlled in a known manner by appropriate choice of the temperature and amount of polymerization initiator for the particular monomers and initiator in an experiment. Once the polymerization temperature has been reached, polymerization continues (step c)) for a further period, for example 2 to 6 hours, in order to complete the reaction of the monomers.

Step a) can be performed according to alternative procedures. For example low shear mixing combined with the addition of surfactants can form an emulsion. Alternatively initial high shear mixing might be used to create the desired particle size followed by low shear agitation with a protective colloid to keep the emulsion dispersed. Additional initiator can be added later in the polymerization to reduce the level of residual monomers. Monomers may be added during the course of the reaction to control dosage. Salts may be added e.g. to buffer the pH.

The emulsion includes a polymerization initiator. Radicals can be generated by thermal decomposition of compounds such as peroxy and azo compounds, or by photolysis with UV radiation or by redox reactions. Suitable Initiators may be soluble in the oil phase and/or the aqueous phase of the emulsion. For example, an initiator may be:
   a thermal polymerization initiator, and/or
   a photopolymerization initiator, and/or
   a redox initiator including a radical-generating reductant/oxidant pair.

Thermal polymerization initiators may be present in an amount comprised between 0.1% and 5% by weight over the combined weight of compounds (I) and (II) in the blend.

Examples of thermal polymerization initiator are:
dilauroyl peroxide,
benzoyl peroxide,
α,α'-azoisobutyronitrile,
2,2'-azobis(2.4-dimethyl valeronitrile),
dimethyl 2,2'-azobis(2-methylpropionate),
1,1'-azo-bis-1-Cyclohexanenitrile,
di-tert-butyl peroxide (CAS: 75-91-2),
potassium persulphate,
ammonium persulfate,
4,4'-azobis(4-cyanovaleric acid),
2,2'-azobis[2-(2-imidazolin-2-yl)propane]dihydrochloride,
2,2'-azobis(2-methylpropionamidine)dihydrochloride,
2,2'-azobis[2-(2-imidazolin-2-yl)propane],
2,2'-azobis[2-methyl-N-(2-hydroxyethyl)propionamide],
   and mixtures thereof.

Photopolymerization initiators may be present in an amount comprised between 0.5% and 5% by weight over the combined weight of compounds (I) and (II) in the blend.

Examples of photopolymerization initiator are:
alpha hydroxyl ketones,
alpha amino ketones,
alpha and beta naphthyl carbonyl compounds,
benzoin ethers such as benzoin methyl ethers,
benzophenone,
acetophenone,
benzaldehyde,
xanthone,
9,10-anthraquinone,
1-hydroxy-cyclohexyl-phenyl-ketone (Irgacure™ 184), and mixtures thereof.

A redox initiator includes a radical-generating reductant/oxidant pair. In the pair
 the oxidant may be present in an amount comprised between 0.01% and 3.0%, such as between 0.02% and 1.0%, or between 0.05% and 0.5% by weight over the combined weight of compounds (I) and (II) in the blend, and/or
 the reductant may be present in an amount comprised between 0.01% and 3.0%, such as between 0.01% and 0.5%, or between 0.025% and 0.25% by weight over the combined weight of compounds (I) and (II) in the blend.

Examples of oxidant for the redox pair are:
salts of peroxodisulfuric acid such as sodium monopersulfate, sodium persulfate, potassium persulphate, ammonium persulfate,
cumene hydroperoxide,
tert-butyl hydroperoxide,
di-tert-amyl peroxide,
tert-butyl peroxybenzoate,
t-amyl hydroperoxide,
hydrogen peroxide, and
mixtures thereof.

Examples of reductant for the redox pair are:
sodium sulphite,
sodium metabisulphite,
sodium formaldehyde sulphoxylate,
ascorbic acid,
sodium dithionite, and
mixtures thereof.

The emulsion includes an emulsifier. The emulsifier includes a protective colloid and may further include a surfactant, and/or a solid particulate colloid (in case a Pickering emulsion is desired). Protective colloids and/or surfactants are conventionally used in emulsion polymerization and in suspension polymerization to stabilize oil-in-water emulsions created by mechanical agitation while the polymerization occurs.

Surfactants are amphiphilic molecules i.e. they consist of a hydrophobic part and a hydrophilic part. The hydrophobic part is generally a hydrocarbon alkyl chain of between 8 to 20 carbon atoms which may be linear or branched and may contain aromatic rings. The hydrophilic part of the molecule can be a non-ionic, anionic cationic or zwitterionic group. Commonly used nonionic hydrophilic groups include polyethoxylated and polypropoxylated groups of different chain lengths typically 3-50 ethylene units long or mixtures of the two, or glycerides or saccharides as either alkyl esters or alkyl ethers. Examples of non-ionic emulsifiers include the Neodol® polyethoxylated alcohols from Shell or the Cremophor® polyethoxylates from BASF or the Plantacare® range of alkyl polyglycosides from Cognis or the sugar esters from Mitsubishi Kagaku Corporation. Anionic hydrophilic parts generally consist of ammonium or alkali metal salts of sulphate, sulphonate, sulphosuccinate, phosphate or carboxylic acid groups. Examples of such surfactants include sodium alkyl benzene sulphonate, sodium alkyl sulphates, dialkyl sulphosuccinates or sodium carboxylates. Cationic surfactants are usually quaternary ammonium salts of halide or methosulphate anions such as monoalkyly trimethyl ammonium chlorides available commercially under the name Praepagen® from Hoescht. The choice of the appropriate surfactant or mixture of surfactants to achieve the desired particle size in the emulsion is known to those skilled in the art and is discussed for example in "Emulsion Science and Technology by T F Tadros et al Wiley-VCH 2009 ISBN 3527325255. A detailed review of surfactants suitable in a process like the one presently disclosed can also be found in WO2010119020, from page 9, line 6 till page 14, line 10. In particular, reference can be made to the alcohol alkoxylates or alcohol phenol alkoxylates of formula (V) and the specific examples thereof disclosed in WO2010119020 page 12, line 19 till page 13, line 13.

A suitable protective colloid has an average molecular weight comprised between 500 and 1,000,000 g/mol, for example between 1,000 and 500,000 g/mol.

Examples of protective colloid are:
cellulose derivatives such as hydroxyethylcellulose, carboxymethylcellulose and methylcellulose,
polyvinylpyrrolidone,
copolymers of N-vinylpyrrolidone,
polyvinyl alcohols obtainable by full to partial hydrolyses of polyvinyl acetates,
polyacrylic and/or polymethacrylic acid,
copolymers of acrylic acid and methacrylic acid,
ionic colloids such as sulphonic-acid-group-containing water-soluble polymers (e.g. 2-acrylamido-2-alkylsulphonic acids and styrene sulphonic acids), and
mixtures thereof.

Advantageously, the protective colloid is a water-soluble protective colloid. Preferably, this means that the colloid has solubility in water of at least 5 g/L at 20° C.

Advantageously, the protective colloid includes at least polyvinyl alcohol (PVA), such as a PVA obtainable by full to partial hydrolyses of polyvinyl acetates.

The protective colloid may be present in an amount comprised between 0.1% and 10% by weight over the weight of the water phase of the oil-in-water emulsion.

Step b) entails inducing decomposition of polymerization initiator. Polymerization may be initiated either in the oil phase (suspension polymerization) or the water phase (emulsion polymerization) of the emulsion depending on the choice of the initiator(s). It is also possible to initiate polymerization in the two phases separately by appropriate choice of initiator and conditions. Step b) may comprise:
 subjecting the oil-in-water emulsion to heat, and/or
 subjecting the oil-in-water emulsion to UV light, and/or
 triggering a redox reaction within the oil-in-water emulsion.

The microcapsules of the invention may also comprise on their surface (e.g. surface grafted) deposition aids, i.e. aids aiming to optimize the deposition of microcapsule on the intended substrate (examples of substrates are hair, skin and fabrics such as cotton). Examples and use of deposition aids on microcapsules are for example disclosed in EP21558474, EP1572767, EP2188364 and EP1019478.

The deposition aid may be present in an amount comprised between 0.1% and 10% by weight over the dry weight of a microcapsule.

The deposition aid may be a polymeric deposition aid. Examples may be synthetic or natural polymers or combinations thereof (e.g. through partial chemical modification of natural polymers).

The deposition aid may be a peptide, a protein, or a chemical derivative thereof, providing for a binding to the intended substrates. For example cellulases bind to cotton while proteases bind to wool, silk or hair.

The deposition aid may be a polysaccharide or a chemical derivative thereof. The polysaccharide preferably has a [beta]-1,4-linked backbone. Examples of polysaccharide are cellulose, a cellulose derivative, or another [beta]-1,4-linked polysaccharide binding to cellulose, such as polymannan, polyglucan, polyglucomannan, polyxyloglucan and polygalactomannan or mixtures thereof. For example, the polysaccharide is selected from the group consisting of polyxyloglucan and polygalactomannan. Highly preferred polysaccharides are selected from locust bean gum, tamarind gum, xyloglucan, non-ionic guar gum, cationic starch and mixtures thereof. For example, the deposition aid is locust bean gum, or chemical derivatives thereof.

In one embodiment, the process presently disclosed may include a step d) to be performed after step c) and including binding a deposition aid to the microcapsules. The deposition aid may be adsorbed to the microcapsule shell or physically and/or chemically bonded to the microcapsule shell. Adsorption (i.e. physical binding) of the deposition aid to the already-formed microcapsule shell may rely on hydrogen bonding, Van Der Waals or electrostatic attraction between the deposition aid and the microcapsule. The deposition aid is thus external to the microparticle and is not, to any significant extent, within the shell and/or within the microcapsule core.

Alternatively, a deposition aid may be part of the emulsion provided in step a). In this case, the deposition aid will be integral part of the microcapsule shell. This situation is known as "entanglement". By entanglement as used herein is meant that the deposition aid is partially buried within the interior of the microcapsule. This is obtained by adding the deposition aid to the emulsion e.g. before the polymerization is triggered. By letting the polymerization propagate, part of the deposition aid remains entrapped and bound in the extending polymer that will form the microcapsule shell whilst the remainder is free to extend into the aqueous phase of the emulsion. In this manner, the deposition aid is only partially exposed at the microcapsule surface.

In one aspect, the present disclosure discloses a water-based dispersion comprising a microcapsule as defined above, for example a plurality of microcapsules as defined above (also referred to as "slurry" or "slurry dispersion").

The water-based dispersion may be obtainable by a free radical polymerization process as defined above.

The dispersion may conveniently be used to prepare e.g. liquid products that will be discussed later in this disclosure. The slurry functions thus as a concentrated fluid which is added to the liquid products. Since this process entails a substantial dilution of the slurry components, microcapsules are contained in the slurry in amounts that are higher than the target amount in the final products. For this reasons, the dispersion may contain microcapsules in amounts of at least 30%, such as at least 40%, or at least 50%, or at least 60%, by weight over the weight of the dispersion (wherein percentage is calculated on the dry dispersion).

The slurry can also conveniently be used as a storage medium for the microcapsules of the invention. In case the microcapsules are stored in the form of aqueous based slurry but no water (or a limited amount of water) must be present in the final product, the slurry can be spray-dried and the spray-dried microcapsules are then added to the final intended product.

The present disclosure discloses a product comprising a microcapsule as defined above. The product may be a non-edible consumer goods product, a household cleaner or laundry product, a personal care product or a cosmetic product.

Conveniently, the product is liquid at room temperature and it has a pH of more than 2, for example more than 4, such as between 2 and 12, for example between 4 and 12.

Unless otherwise indicated, non-edible means non-intended for ingestion by humans or animals. This includes non-food products that may accidentally be swallowed during normal use. Notably, included within the definition of non-edible products are products for dental and oral care, such as toothpastes, mouth washes and lip balms which although not intended for ingestion may nevertheless accidentally enter the gastro-intestinal tract.

The formulations and ingredients of liquid household, laundry, personal care and cosmetic products in which microcapsules of the invention may be used are well known to those skilled in the art, reference may be made to the following works:

Formulating Detergents and Personal Care Products A guide to Product Development by L Ho Tan Tai, ISBN 1-893997-10-3 published by the AOCS Press Volume 67 of the Surfactant Science Series Liquid Detergents ISBN 0-8247-9391-9 (Marcel Dekker Inc), Harry's Cosmeticology published by CHS Press 8th Edn. 2000 ISBN 0820603724.

Personal care and cosmetic products may include products that can be applied to the skin, hair and nails either as leave on or rinse off product. Personal care and cosmetic products include powders, creams, emulsions, lotions, gels and oils for the skin (face, hands, feet etc), tinted bases (liquids and pastes) and liquid impregnated tissues; products for applying and removing make-up from the face and eyes; hair care products including hair tints and bleaches; products for waving, straightening, setting and fixing hair; shaving products including creams, foams mousses and depilatory products; sun bathing products and products for tanning without the sun; deodorant and antiperspirant products.

Advantageously a personal care or cosmetic product is selected from the group consisting of a shaving aid, a shampoo, a hair-conditioner product, a leave-on-skin-care product, a skin cleansing or washing product (such as a rinse-off skin cleansing or washing product), a moist tissue and a body spray, deodorant or antiperspirant.

Shaving aids specifically include foams, gels, creams and bars (reference can be made for example to U.S. Pat. Nos. 7,069,658, 6,944,952, 6,594,904, 6,182,365, 6,185,822, 6,298,558 and 5,113,585).

Shampoos and hair conditioners specifically include two-in-one shampoos and shampoos especially formulated for dry or greasy hair or containing additives such as antidandruff agents. Hair conditioners may be rinse off or leave on hair conditioners also included are hair tonics, bleaches colorants, setting and styling products. Reference can be made for example to U.S. Pat. Nos. 6,162,423, 5,968,286, 5,935,561, 5,932,203, 5,837,661, 5,776,443, 5,756,436, 5,661,118, 5,618,523.

Leave-on-skin-care products comprise skin washing products, moist tissues, body sprays, deodorants and antiperspirants.

Skin washing products specifically include beauty and hygiene bar soaps, shower gels, liquid soaps, body washes, exfoliating gels and pastes (reference can be made for example to U.S. Pat. Nos. 3,697,644; 4,065,398; 4,387,040).

Moist tissues (wipes) specifically include skin cleansing wipes, baby wipes, make-up removal wipes and skin refreshing wipes (reference can be made for example to U.S. Pat. No. 4,775,582; WO02/07701; WO2007/069214 and WO95/16474).

Body sprays, deodorants and antiperspirants specifically include sticks, liquid roll-on applicators and pressurized sprays.

Examples of household cleaners and laundry products are:
hard surface cleaners such as cleaners for floors, solid work surfaces, tiled surfaces, crockery by hand or machine washing and mirrors and glass,
soft furnishing treatments such as liquid cleaners and refresher products such as odour treatment agents as exemplified by Febreze® (P&G),
powdered laundry detergents, detergent tablets and bars, laundry detergent liquids include light duty liquids, heavy duty liquids, concentrated liquid detergents, non or low aqueous laundry liquids and more specialised cleaners for woollen or dark garments,
fabric softeners and pre- and post-wash treatments such as tumble drier sheets, ironing waters and wash additives.

Advantageously, a laundry product is selected from the group consisting of a fabric softener, a fabric conditioner and a laundry detergent.

Household cleaners may be in the form of cream cleaners, isotropic liquid cleaners, spray cleaners and pre-moistened surface cleaning wipes (reference can be made for example to WO91/08283, EP743280, WO96/34938, WO01/23510, and WO99/28428).

Fabric softeners and conditioners specifically include both conventional diluted (e.g. 2% to 8% by weight of softener in the product) liquid active concentration softeners and concentrated (e.g. 10% to 40% by weight of softener in the product) liquid active concentration softeners as well as fabric conditioners which may contain ingredients to protect colors or garment shape and appearance (reference can be made for example to U.S. Pat. Nos. 6,335,315, 5,674,832, 5,759,990, 5,877,145, 5,574,179).

Laundry detergents, particularly liquid laundry detergents, specifically include light duty liquid detergents and heavy duty liquid detergents which may be structured multiphase liquids or isotropic liquids and which may be aqueous or non-aqueous liquids. These liquids may be in bottles or unit dose sachets and they may optionally contain bleaching agents or enzymes (reference can be made for example to U.S. Pat. Nos. 5,929,022, 5,916,862, 5,731,278, 5,470,507, 5,466,802, 5,460,752, and 5,458,810).

The products presently disclosed may contain water and/or surface active material, either as an emulsifier, if the product is an emulsion, or as a detergent active material if the product has some kind of cleaning function. In certain embodiments the concentration of surface active material in the product will be within the range 0.1-60% by weight; usually the level of surface active material will be 50% by weight or lower; for most products the level of surface active material will be 30% by weight or lower. On the other hand, the level of surface active material will usually be at least 0.1% by weight preferably greater than 1.0% and more preferably greater than 3.0% by weight. Certain product formulations are water sensitive (e.g. anti-perspirant, deodorant formulations, non-aqueous liquids packaged in water soluble polyvinyl alcohol films), and for these applications it may be desirable to spray dry the microcapsules to remove water, before the microcapsules are incorporated in the product formulation. For products which have a cleaning function it is likely the level of surface active material will be higher, typically greater than 10% by weight and preferably greater than 15% by weight. All percentages are expressed by weight over the weight of the product.

Examples of leave-on products containing emulsifiers are: hand and body lotions, make up removing lotions, skin creams, sunscreen products and sunless tanning products and domestic freshener sprays. Also included are articles of manufacture impregnated with liquids, for example pads or wipes impregnated with lotions for make-up application or removal, or to apply sunscreen compounds or sunless tanning agents, for personal cleansing e.g. as moist toilet tissue or baby wipes.

Examples of personal cleansing products containing detergents are: shampoos, body washes, liquid soaps. Some cleaning products may be considered leave on products even though they are used for cleansing if there is no rinsing or further cleaning action after use. Baby wipes are an example, although used for cleaning the liquid deposited on the skin is not removed by rinsing.

The non-rinsed cosmetic, toiletry and personal care compositions described herein can contain various emulsifiers which are useful for emulsifying the various components of the products. Suitable emulsifiers can include any of a wide variety of non-ionic, cationic, anionic, and zwitterionic surface active materials as disclosed in publications such as McCutcheon's, Detergents and Emulsifiers, North American Edition (1986), published by Allured Publishing Corporation and in the following patents: U.S. Pat. Nos. 5,011,681; 4,421,769; and 3,755,560.

Experimental evidence shows that the composition of certain products such as setting lotions, eau de toilettes, body spray aerosols, hair foams, which contain short hydrocarbon chain alcohols may negate the benefit brought about by the microcapsules presently disclosed. Therefore, it is preferable that the products do not contain significant amounts (e.g. more than 2.5% or more than 5%, such as more than 10%, or more than 20% or more than 50% or more than 70% by weight over the weight of the product) of short hydrocarbon chain alcohols such as aliphatic $C_1$-$C_4$ alcohols (e.g. ethanol or isopropanol). Without wishing to be bound by any theory, it is believed that short hydrocarbon chain alcohols might affect the microcapsule integrity thereby facilitating the leakage of the perfume content.

Microcapsules amount into liquid household, laundry, personal care and cosmetic products may vary depending on several aspects such as the desired microcapsule concentration, the proportion of fragrance within the microcapsule and the amount of fragrance necessary to create the olfactory effect desired. After removing all liquid components from a given product (i.e. measured as dry weight) the microcapsules of the present disclosure may be present from 0.01 to 10% by weight, preferably from 0.05% to 2.5% by weight, more preferably from 0.1 to 1.25% by weight over the weight of the product. The microcapsules may be incorporated into the products by any conventional means, usually as a water-based liquid dispersion added at a suitable stage in the product manufacturing process but usually after any high shear mixing stage. If liquid at room temperature, it is preferable that the product into which the microcapsules are to be added has a viscosity greater than 20 Mpas, for example greater than 100 Mpas, or greater than 1,000 Mpas, or even greater than 10,000 Mpas, when measured at a low (e.g. 10rpm) spindle speed. Conveniently, the product shows shear thinning rheology. If necessary, viscosity can be adjusted through the addition of conventional viscosity modifying agents. Suitable agents as well as equipment and conditions to measure the viscosity of a product are discussed in Rheology Modifiers Handbook Practical Uses and Applications by M R Rosen and D Braun published by William Andrew Publishing in 2000 with ISBN 978-0-8155-1441-1.

Further embodiments and advantages of the present invention will become apparent to a skilled reader in light of the examples provided below.

General Manufacturing Procedure (Suspension Free Radical Polymerization):

An aqueous phase was prepared by dissolving 4.0 g of poly(vinyl alcohol), hydrolyzed to 87-89%, $M_w$=85000-124000 g/mol, in 196.0 g of water. An oil phase was prepared by mixing 85.0 g of a given fragrance, the blend compounds and the initiator (0.9 g of lauroyl peroxide for samples 1 to 8 and 10 to 12, 0.6 g of Dimethyl 2,2'-azobis (2-methylpropionate) for sample 9). This mixture was stirred until complete dissolution of the initiator. The aqueous phase and the oil phase are placed into a 500 mL-batch reactor equipped with a condenser, a thermometer, a nitrogen inlet and a deflocculating blade (diameter 4 cm). During the process, the mixture is stirred at 900 rpm and nitrogen is bubbled through the mixture to remove oxygen. First, the mixture is heated from room temperature to 35° C. within 20 min and kept at 35° C. for 1 hour. The resultant emulsion is then heated to 70° C. within 30 min and kept at 70° C. for 4 hours. Finally, the resultant microcapsule dispersion is cooled to room temperature within 1 hour. The mean particle size of the resultant microcapsule dispersion is determined by laser diffraction (volume median diameter (D(v, 0.5)).

Leakage Test Manufacturing Procedure

To evaluate the leakage associated to the choice of a specific crosslinker (compound (II)) as presently disclosed, the following manufacturing is followed. An aqueous phase is prepared by dissolving 4.0 g of poly(vinyl alcohol), hydrolyzed to 87-89%, Mw=85000-124000 g/mol, in 196.0 g of water. An oil phase is prepared by mixing 85.0 g of fragrance no. 1; 14.5 g of 2-hydroethyl methacrylate, 17.7 g of crosslinker (compound II), 0.9 g of lauroyl peroxide. This mixture is stirred until complete dissolution of the lauroyl peroxide. The aqueous phase and the oil phase are placed into a 500 mL-batch reactor equipped with a condenser, a thermometer, a nitrogen inlet and a deflocculating blade (diameter 4 cm). During the process, the mixture is stirred at 900 rpm and nitrogen is bubbled through the mixture to remove oxygen. First, the mixture is heated from room temperature to 35° C. within 20 min and kept at 35° C. for 1 hour. The resultant emulsion is then heated to 70° C. within 30 min and kept at 70° C. for 4 hours. Finally, the resultant microcapsule dispersion is cooled to room temperature within 1 hour.

Capsule Particle Size Measurement

Median volume diameter and span were measured with a laser diffraction/scattering particle size distribution analyzer (trade name: LA-950V2, manufactured by Horiba, Ltd.). The dispersant was 18 MΩ water. Several droplets of the emulsion or the capsule dispersion were poured into the flow cell unit until an acceptable level of laser light obscuration was achieved and triplicate measurements were then performed. For the calculation of the particle size measurement, the refractive indexes were set at 1.33 (for the water dispersant) and 1.47 (for the fragrances and the poly(methacrylate) capsules). The median capsule diameter was measured as a particle size of 50% frequency (median size) on a volumetric basis The span was calculated as discussed below. Since the particle size may be larger than 10 µm the analysis of the results by the Fraunhofer approximation (opaque particles, geometrical optic rules) is also relevant and lead valid size determination. In this case the refractive index is not necessary.

Span values were calculated according to the following formula:

$$\text{Span} = \frac{D(v; 0.9) - D(v; 0.1)}{D(v; 0.5)}$$

in which D(v; 0.9) is the particle size for 90% of the microcapsules by volume, D(v; 0.1) is the particle size for 10% of the microcapsules by volume and D(v; 0.5) is the median volume microcapsule size as previously defined.

Solid Content Measurement Method

Approximately 3 g of slurry are weighted in an aluminum weighing dish and dried during two hours at 105° C. in order to remove water. The weight of the dry sample is then determined at room temperature and compared to the weight of the dispersion.

| | (% by weight): |
|---|---|
| Composition of fragrance no. 1 | |
| Isobornyl acetate (CAS No 125-12-2): | 25 |
| Camphor gum powder synthetic (CAS No 464-49-3): | 15 |
| Lilial (CAS No 80-54-6): | 15 |
| Eucalyptol (CAS No 470-82-6): | 8 |
| Ethyl-2-methylpentanoate (CAS No 39255-32-8): | 6 |
| Cedrol (CAS No 77-53-2): | 6 |
| Allyl heptoate (CAS No 142-19-8): | 5 |
| Styrallyl acetate (CAS No 93-92-5): | 5 |
| 2-Methylundecanal (CAS No 110-41-8): | 5 |
| Vertenex (CAS No 32210-23-4): | 5 |
| Coumarin (CAS No 91-64-5): | 3 |
| Delta damascone (CAS No 57378-68-4): | 2 |
| Composition of fragrance no. 2 | |
| Isobornyl acetate (CAS No 125-12-2): | 29 |
| Verdox (CAS No 88 41 5) | 29 |
| Camphor gum powder synthetic (CAS No 464-49-3): | 14 |
| 2-methyl undecanal (CAS No 110-41-8): | 14 |
| Undecalactone gamma (CAS No 104-67-6): | 14 |
| Composition of fragrance no. 3 | |
| Isobornyl acetate (CAS No 125-12-2): | 10 |
| Verdox (CAS No 88 41 5) | 10 |
| Camphor gum powder synthetic (CAS No 464-49-3): | 10 |
| Undecalactone gamma (CAS No 104-67-6): | 10 |
| ethyl 2-methyl pentanoate (CAS No 39255-32-8): | 10 |
| Dimethyl benzyl 35arbonyl acetate (CAS No 151-05-3): | 10 |
| ethyl 2-methylbutyrate (CAS No7452-79-1): | 10 |
| Eucalyptol (CAS No 470-82-6): | 10 |
| Styrallyl acetate (CAS No 93-92-5): | 10 |
| 2-methyl undecanal (CAS No 110-41-8): | 5 |
| Phenyl ethyl methyl ether (CAS No 3558-60-9): | 5 |
| Composition of fragrance no. 4 | |
| Isobornyl acetate (CAS No 125-12-2): | 10 |
| Verdox (CAS No 88 41 5): | 10 |
| Camphor gum powder synthetic (CAS No 464-49-3): | 10 |
| Undecalactone gamma (CAS No 104-67-6): | 10 |
| Dihydroterpinyl acetate (CAS No: 58985-18-5): | 10 |
| Hedione (CAS No: 24851-98-7): | 10 |
| Galaxolide (CAS No 1222-05-5): | 10 |
| Cedramber (CAS No 19870-74-7): | 10 |
| 2-Methylundecanal (CAS No 110-41-8): | 5 |

-continued

| | (% by weight): |
|---|---|
| Cyclamen aldehyde (CAS No 103-95-7): | 5 |
| Exaltolide (CAS No 106-02-5): | 5 |
| Undecanal (CAS No 112-44-7): | 5 |

EXAMPLE 1

Samples 1 to 12

Using the general manufacturing procedure discussed above, the following samples 1 to 12 were prepared:
Monomer Abbreviations:
HEMA: 2-hydroxyethyl methacrylate
MMA: methyl methacrylate
BDMA: 1,4-butanediol dimethacrylate
EGDMA: ethylene glycol dimethacrylate
PDMA: 1,3-propanediol dimethacrylate

| Sample number | Fragrance | Blend in the oil phase (%) | Composition of the monomer blend (%) | | | Median volume diameter (μm) Span | Solid content (%) |
|---|---|---|---|---|---|---|---|
| | | | Monomer (Ia) | Monomer (Ib) | Compound (II) | | |
| 1 | 1 | 27.3 | HEMA: 45 | / | BDMA: 55 | 30.6 0.81 | 38.9 |
| 2 | 1 | 27.3 | HEMA: 45 | / | PDMA: 55 | 43.6 1.02 | 39.6 |
| 3 | 1 | 27.3 | HEMA: 45 | / | EGDMA: 55 | 38.0 0.99 | 40.5 |
| 4 | 1 | 27.3 | HEMA: 40 | MMA: 5 | BDMA: 55 | 35.0 0.91 | 38.4 |
| 5 | 1 | 27.3 | HEMA: 40 | MMA: 16 | BDMA: 44 | 37.6 1.00 | 35.7 |
| 6 | 1 | 35.0 | HEMA: 40 | MMA: 27 | BDMA: 33 | 35.1 0.84 | 39.0 |
| 7 | 1 | 27.3 | HEMA: 33 | MMA: 27 | BDMA: 40 | 34.0 0.96 | 36.5 |
| 8 | 1 | 27.3 | HEMA: 25 | MMA: 25 | BDMA: 50 | 37.0 1.01 | 33.3 |
| 9 | 1 | 27.3 | HEMA: 45 | / | BDMA: 55 | 37.8 0.84 | 39.2 |
| 10 | 2 | 27.3 | HEMA: 45 | / | BDMA: 55 | 72 1.7 | 38.9 |
| 11 | 3 | 27.3 | HEMA: 45 | / | BDMA: 55 | 35.8 0.89 | 38.2 |
| 12 | 4 | 27.3 | HEMA: 45 | / | BDMA: 55 | 45.7 0.87 | 39.6 |

EXAMPLE 2

Comparative Example (Sample 13)

The same procedure as in example 1 was repeated but without monomer (Ia). An aqueous phase was prepared by dissolving 4.0 g of poly(vinyl alcohol), hydrolyzed to 87-89%, $M_w$=85000-124000 g/mol, in 196.0 g of water. An oil phase was prepared by mixing 85.0 g of fragrance no. 1, 13.7 g of 1,4-butane diol dimethacrylate, 13.1 g of methacrylic acid and 5 .2 g of methyl methacrylate and 0.9 g of lauroyl peroxide. This mixture was stirred until complete dissolution of the lauroyl peroxide. The aqueous phase and the oil phase were placed into a 500 mL-batch reactor equipped with a condenser, a thermometer, a nitrogen inlet and a deflocculating blade (diameter 4 cm). During all the process, the mixture was stirred at 900 rpm and nitrogen was bubbled through the mixture to remove oxygen. First, the mixture was heated from room temperature to 35° C. within 20 min and kept at 35° C. for 1 hour. The resultant emulsion was then heated to 70° C. within 30 min and kept at 70° C. for 4 hours. Finally, the resultant microcapsule dispersion was cooled to room temperature within 1 hour. The mean particle size of the resultant microcapsule dispersion was determined by laser diffraction (Volume median diameter (D(v, 0.5)).

| Sample number | Fragrance | Median volume diameter (μm) Span | Solid content (%) |
|---|---|---|---|
| 13 | 1 | 38.6 1.0 | 39.6 |

EXAMPLE 3

Samples 14 and 15

An aqueous phase was prepared by dissolving 4.0 g of poly(vinyl alcohol), hydrolyzed to 87-89%, $M_w$=85000-124000 g/mol, in 196.0 g of water. An oil phase was prepared by mixing 85.0 g of fragrance no. 1, 10.0 g of 2-hydroxyethyl methacrylate, 5.0 g of a second monomer (Ia), 17.5 of 1,4-butane diol dimethacrylate and 0.6 g of lauroyl peroxide. This mixture was stirred until complete dissolution of the initiator and of the second monomer (Ia), if it is a solid. The aqueous phase and the oil phase are placed into a 500 mL-batch reactor equipped with a condenser, a thermometer, a nitrogen inlet and a deflocculating blade (diameter 4 cm). During the process, the mixture is stirred at 900 rpm and nitrogen is bubbled through the mixture to remove oxygen. First, the mixture is stirred at 20° C. for 30 min. The resultant emulsion is then heated to 70° C. within 1 hour and kept at 70° C. for 3 hours. Finally, the resultant microcapsule dispersion is cooled to room temperature within 1 hour. The mean particle size of the resultant microcapsule dispersion is determined by laser diffraction (volume median diameter (D(v, 0.5))).

during 3 hours. Finally, the resultant microcapsule dispersion was cooled to room temperature within 1 hour. The mean particle and the span number of the resultant microcapsule dispersion were determined according to the capsule particle size measurement method disclosed below.

| Sample number | Polymerization initiator | Monomer (Ic) | Temperatures T1 | T2 | Median volume diameter (μm) Span | Measured solid content (Theoretical solid content) (%) |
|---|---|---|---|---|---|---|
| 16 | Lauroyl peroxide:1.5 g | MAPTAC | 20 | 70 | 37.9 0.61 | 46.1 (46.9) |
| 17 | Benzoyl peroxide:1.23 g | MAPTAC | 20 | 80 | 47.2 0.73 | 46.5 (46.9) |
| 18 | Benzoyl peroxide:1.23 g | Solution of MAPTAC at 50% in water: 6.5 g | 20 | 80 | 41.1 0.60 | 46.2 (46.9) |

| Sample number | Second monomer (Ia) | Median volume diameter (μm) Span | Measured solid content (Theoretical solid content) (%) |
|---|---|---|---|
| 14 | Glycidyl methacrylate | 49.3 0.94 | 37.3 (38.4) |
| 15 | Poly(ethylene glycol)methyl ether methacrylate $M_n$ = 950 g/mol | 36.9 0.92 | 39.3 (38.4) |

EXAMPLE 4

Samples 16, 17 and 18

A 10% poly(vinyl alcohol) aqueous solution was prepared in advance by dissolving poly(vinyl alcohol), hydrolyzed to 87-89%, $M_w$=85000-124000 g/mol in water. In 200 g of water with a pH between 6.5 and 8.5, were introduced in the following order: 24.0 g of 2-hydroxyethyl methacrylate, 0.5 g of a 1% solution of MAPTAC in water and 1.23 g of Aerosil® 200 silica. The dispersion was stirred during 30 min. An oil phase was prepared by mixing 150 g of fragrance no. 1, 29 g of 1,4-butane diol dimethacrylate and a polymerization initiator. This mixture was stirred until complete dissolution of the polymerization initiator. The oil phase and the dispersion of silica in water were stirred together at 10000 rpm for 1 min using a high-shear mixer (Ystral X 10/20 E3-1050 W equipped with a Dispermix head of diameter 40/54 mm). At this stage, the resultant emulsion had a span number below 0.75. The emulsion was placed into a batch reactor equipped with a condenser, a thermometer, a nitrogen inlet and an anchor stirrer. A known amount of 10% poly(vinyl alcohol) aqueous solution is added to get a total weight concentration of poly(vinyl alcohol) in the water phase of 2.6% and the mixture was stirred during 10 min. In sample 18, a further amount of MAPTAC was then added (see table below for details). During the following of the process, the mixture was stirred at 250 rpm and nitrogen was bubbled through the mixture to remove oxygen. The temperature is first fixed at a temperature T1 during 30 min and the temperature is then increased to the temperature T2 within one hour. The mixture is kept at this temperature T2

Leakage Test Method

The fragrance leakage is the ratio of fragrance released in the base to the encapsulated fragrance. The fragrance released in the fabric softener and the amount of encapsulated fragrance in the slurry are determined through extraction with solvent and analysis by gas chromatography.

Procedure for the Determination of the Encapsulated Fragrance

The slurry is first homogenized by stirring with a spatula. 150 mg of slurry are withdrawn. 20 mL of ethanol and 100 μL of an internal standard solution are added. The mixture is left in an ultrasonic bath for 30 minutes. The mixture is filtered on a 0.45 μm Acrodisc filter and then analyzed by GC/FID (gas chromatography equipped with a flame ionization detector). Integration areas are determined from the FID signal using Agilent® Chemstation software. Three replicate samples are extracted and analyzed. The internal standard solution is a solution of methyl decanoate in ethanol at a concentration of 100 mg/mL.

Procedure for the Determination of the Fragrance Released in the Base

A mixture of the water dispersion containing 38.4% by weight of microcapsules (% expressed over the weight of the dried slurry) and a liquid base (see below for compositions) is prepared and stored in a glass bottle in an oven at the controlled temperature of 40° C. for 1/2/4/8 weeks. The final concentration of the water dispersion of microcapsules is 0.5% by weight for application in fabric softener and laundry detergent, and 1% by weight for other applications. After each time of storage, the mixture is shaken and 10 g are withdrawn. This sample is centrifuged to separate the liquid from the capsules. 1 g of centrifuged liquid is mixed with 1 g of celite (diatomaceous earth). 545.5 mL of pentane and 50 μL of an internal standard solution (see below for composition) are added. The mixture is agitated on a roller bed for 1 hour. The supernatant is then injected in GC/FID (gas chromatography apparatus using a flame ionization detector). Integration areas are determined from the FID signal using Agilent® Chemstation software. Each extract is analyzed three times.

The internal standard solution is a solution of methyl decanoate in hexane at a concentration of 10 mg/mL.

The fragrance leakage of the capsules was determined in different liquid bases:

Fabric softener: Commercial product Le Chat® 0% (pH=2.8)

Liquid laundry detergent: Commercial product Persil®
  0% (pH=8.0)
Shampoo bases
  Shampoo base without silicone (pH=5.2)
  Shampoo base with silicone (pH=4.3)
Shower gel bases
  Shower gel (pH=4.5)
  Shower gel (pH=5.8, test liquid base)
Make-up remover base (pH=7.6)

The procedure referred to in the present application as leakage test method corresponds to the method for determining the fragrance leakage as discussed above wherein the composition of the liquid base (i.e. the test liquid base) is the one of the shower gel base having pH 5.8 as defined below.

Instrumentation:
Agilent® 6890 GC connected to Chemstation software
Column: HP-5MS, 30 m×0.25 mm×0.25 µm
Oven temperature: 50° C. for 2 min then heat to 280° C. at 10° C./min and hold at 280° C. for 5 min.
Injector: 250° C., Detector: 250° C.
24 injection volume (splitless)
Calculations:
Determination of the weight of leaked fragrance component i in the sample:

$$W_{perf,i} = \frac{A_{perf,i} \times w_{IS}}{A_{IS}}$$

$W_{perf,i}$: weight of leaked fragrance component i (mg)
$A_{perf,i}$: fragrance component i area
$A_{IS}$: weight of internal standard (mg)
$A_{IS}$: internal standard area
Determination of the weight of leaked fragrance in the sample:

$$W_{frag} = \sum_i W_{perf,i}$$

$W_{frag}$: weight of leaked fragrance (mg)
Determination of the percentage of the fragrance leakage:

$$\% \text{ leakage}_{frag} = \frac{W_{frag}}{W_{tot\ frag}} \times 100$$

% leakage$_{frag}$: percentage of fragrance leakage
$W_{tot\ frag}$: weight of encapsulated fragrance in the capsule dispersion determined experimentally
Determination of the percentage of leakage of fragrance component i:

$$\% \text{ leakage}_{perf} = \frac{W_{perf}}{W_{tot\ perf}} \times 100$$

% leakage$_{perf}$: percentage of leakage of fragrance component i.
$W_{tot\ perf}$: weight of encapsulated fragrance component i in the capsule dispersion determined experimentally Composition of Liquid Bases
Composition of the shampoo base without silicone (a 30% citric acid aqueous solution was added to adjust the pH at 5.2)

| Raw material | % (w/w) in the formula | INCI name |
|---|---|---|
| Water | 72.8 | AQUA |
| Texapon N70 | 13.57 | SODIUM LAURETH SULFATE (70%) |
| Miranol C2M | 7.86 | DINA COCOAMPHODIACETATE (38.9%) |
| Euperlan PK 3000 | 1.82 | Glycol Distearate/LAURETH-4/CAPB (44%) |
| Sodium chloride | 1.20 | SODIUM CHLORIDE |
| Tegosoft GC | 1 | PEG-7 GLYCERYL COCOATE |
| D panthenol 75L | 0.5 | PANTHENOL |
| Sodium benzoate | 0.5 | SODIUM BENZOATE |
| Celquat SC 230M | 0.35 | POLYQUATERNIUM-10 |
| Niacinamide PC | 0.2 | NIACINAMIDE |
| Salicylic acid | 0.2 | SALICYLIC ACID |

Composition of the shampoo base with silicone (pH=4.3)

| Raw materials | % (w/w) in the formula | INCI name |
|---|---|---|
| Water | 55.54 | AQUA |
| Texapon NSO IS | 23.39 | SODIUM LAURYL ETHER SULFATE (70%) |
| Miranol C2M | 7.86 | DISODIUM COCOAMPHODIACETATE |
| Mirasil DME 2 | 6.25 | DIMETHICONE MICROEMULSION |
| Citric acid | 1.90 | CITRIC ACID (50%) |
| Tegin BL 315 | 1.00 | GLYCOL DISTEARATE |
| Polypropylene glycol | 1 | POLYPROPYLENE GLYCOL |
| Procetyl AWS | 0.9 | PPG-5 CETETH 20 |
| Sodium hydroxide | 0.56 | SODIUM HYDROXIDE |
| Carbopol 980NF | 0.50 | CARBOMER |
| Sodium benzoate | 0.5 | SODIUM BENZOATE |
| Nipagin M sodium | 0.2 | SODIUM METHYL PARABEN (98.5%) |
| DL alpha tocopherol | 0.10 | TOCOPHEROL |
| Uvinul MC80 | 0.10 | ETHYLHEXYL METHOXYCINNAMATE |
| Jaguar C13S | 0.10 | GUAR HYDROXYPROPYLTRIMONIUM CHLORIDE |
| Uvinul M40 | 0.05 | BENZOPHENONE-3 |
| Sodium chloride | 0.05 | SODIUM CHLORIDE |

Composition of the shower gel (a 30% citric acid aqueous solution was added to adjust the pH at 4.5 or 5.8. The version having pH 5.8 is the test liquid base mentioned in the leakaae test method)

| Raw material | % (w/w) in the formula | INCI name |
|---|---|---|
| Water | 69.64 | AQUA |
| Texapon N70 | 14.24 | SODIUM LAURYL ETHER SULFATE 68.8% |
| Dehyton AB 30 | 6.00 | COCOBETAINE (30%) |
| Pricerine 9091 | 1.80 | GLYCERINE (99.5%) |
| Miranol C2M | 1.57 | DISODIUM COCOAMPHODIACETATE |
| Tegin BL350 | 1.20 | GLYCOL DISTEARATE |
| Merquat S | 1.11 | POLYQUATERNIUM-7 (8.5-9.5%) |
| Comperlan | 0.8 | CMEA |
| Carbopol AQUA SF1 | 0.97 | ACRYLATE COPOLYMER (30.9%) |
| Procetyl AWS | 0.90 | PPG-5 CETETH 20 |
| Sodium chloride | 0.75 | SODIUM CHLORIDE |
| Sodium hydroxide 30% | 0.3 | SODIUM HYDROXIDE (30%) |

-continued

| Raw material | % (w/w) in the formula | INCI name |
|---|---|---|
| Nipaguard DMDMH | 0.27 | DMDM HYDANTOIN |
| Dissolvine Na 2 | 0.25 | DISODIUM EDTA |
| Nipagin M sodium | 0.10 | SODIUM METHYL PARABEN |
| Nipagin M | 0.1 | METHYL PARABEN |

Composition of the make-up remover base (triethanolamine was added to adjust the pH at 7.2):

| Materials | INCI | % w/w |
|---|---|---|
| Water | Water | 87.5 |
| Emulgade CM | Cetearyl Isononanoat/Ceteareth-20/Cetearyl Alcohol/Glyceryl Stearate/Glycerin/Ceteareth-12/Cetyl Palmitate | 10.0 |
| Pricerin 9091 | Glycerin | 2.0 |
| Sepicid HB | Phenoxyethanol/Methylparaben/Ethylparaben/Propylparaben/Butylparaben | 0.5 |

EXAMPLE 5

Fragrance Leakage Results

Composition of the shampoo base without silicone (a 30% citric acid aqueous solution was added to adjust the pH at 5.2)

| Fragrance leakage (%) after different times of storage at 40° C. | | Samples | | | | |
|---|---|---|---|---|---|---|
| (weeks) | | 1 | 2 | 3 | 5 | 13 |
| Commercial concentrated fabric softener Le Chat ® 0% (pH = 2.8) | 0 | 0.7 | 0.6 | 0.5 | 1.3 | 1.2 |
| | 4 | 26.5 | 19.8 | 28.7 | 40.2 | 15.6 |
| Commercial concentrated liquid laundry detergent base Persil 0% (pH = 8.0): | 0 | 1.3 | 1.0 | 1.6 | 1.6 | 3.9 |
| | 4 | 28.7 | 27.6 | 38.4 | 45.6 | 68.6 |
| Shampoo base without silicone (pH = 5.2) | 0 | 1.3 | / | / | / | 0.8 |
| | 4 | 25.7 | / | / | / | 9.2 |
| Shampoo base with silicone (pH = 4.3) | 0 | 1.4 | / | / | / | 0.7 |
| | 4 | 26.2 | / | / | / | 9.1 |
| Shower gel base (pH = 4.5) | 0 | 3.6 | / | / | / | 1.9 |
| | 4 | 34.6 | / | / | / | 14.1 |
| Shower gel base (pH = 5.8) | 0 | 2.6 | / | / | / | 3.1 |
| | 4 | 31.8 | / | / | / | 18.7 |
| Make-up remover base (pH = 7.2) | 0 | 4.0 | / | / | / | 3.5 |
| | 4 | 44.3 | / | / | / | 49.6 |

Perfume Intensity Sensory Test

The intensity of the fragrance was then assessed by a panel of trained assessors familiar with the odour of the test fragrances as a blind experiment. Samples were assessed for strength before and after they were rubbed against hands. Each panelist assessed a fresh set of cloths. Scores were given on an interval scale from 0 (non-noticeable scent) to 4 (very strong scent).

EXAMPLE 6

Olfactory Performances of the Capsules on the Invention on Cotton Toweling Mitts (before Rubbing-after Rubbing). Results

| Sample | Application in fabric softener (Notes: Before rubbing-After rubbing (/4)) | Application in liquid laundry detergent (Notes: Before rubbing-After rubbing (/4)) |
|---|---|---|
| 1 | 0-3.5 | 0-3 |
| 2 | 0-1 | 0-1 |
| 3 | 0-2.5 | 0.5-1.5 |
| 4 | 0-2 | 0-1 |
| 5 | 0-3 | 0-0.5 |
| 6 | 0-3 | 0-1 |
| 7 | 0-2 | 0-1.5 |
| 8 | 0-2 | 0.5-2 |
| 9 | 0-3.5 | 0-2 |
| 10 | 0-3.5 | 0-2 |
| 11 | 0-3.5 | 0-3 |
| 12 | 0-4 | 0-1 |
| 13 | 0-4 | 0-0 |
| 14 | 0-1 | 0-0.5 |
| 15 | 0-1.5 | 0-0.5 |
| 16 | 0-3.5 | 0-2 |
| 17 | 0-3 | 0-1.5 |
| 18 | 0-4 | 0-2.5 |

This example shows that capsules of samples 1-12 and 14-18 provide good olfactive performances on fabrics when they are freshly applied in a fabric softener (acid pH) or a liquid laundry detergent (basic pH) and used in a washing process. On the other hand, the comparative sample 13 provides good olfactory performances in a fabric softener use but no olfactory performances in a liquid laundry detergent use.

These results show that, irrespective of the presence of other variables potentially impacting the leakage (e.g. surfactants, dimethicone and other hydrophobic ingredients in the base), the capsules of the invention display an acceptable fragrance leakage which is independent of the pH of the liquid medium. By contrast, a capsule containing relevant amounts of a ionizable monomer as methacrylic acid (sample 13) leaks differently depending on the pH of the liquid medium.

EXAMPLE 7

Effect of the Crosslinker

Following the general manufacturing procedure identified above, samples 19 and 20 were prepared using fragrance 1 and a proportion of the blend in the oil phase of 27.3%. The table below shows the results of synthesis and of olfactory performances of the capsules of the invention on cotton toweling mitts after a washing machine cycle.

| Sample number | Composition of the monomer blend (%) | | | Median volume diameter (μm) Span | Solid content (%) | Application in liquid laundry detergent (Notes: Before rubbing-After rubbing (/4)) |
|---|---|---|---|---|---|---|
| | Monomer (Ia) | Monomer (Ib) | Compound (II) | | | |
| 19 | HEMA: 45 | / | Ethoxylated pentaerythritol tetramethacrylate (Sartomer ®): 55 | 43.9 0.99 | 38.9 | 0-0 |
| 20 | HEMA: 45 | / | Tricyclododecane dimethanol dimethacrylate (Sartomer ®): 55 | 42.0 1.17 | 37.6 | 0-0 |

When compared e.g. to the results scored by samples 1-3 and 9-12 in Example 6, the results of samples 19 and 20 confirm that the choice of the crosslinker has per se a technical effect and that the preferred crosslinkers, as presently disclosed, may bring an advantage in terms of capsule shell resistance.

This application is based on European Patent Application No. 13306095.4 filed on Jul. 29, 2013, the entire subject matters of which are incorporated herein by reference. In addition, the subject matters of all documents cited in the specification are also incorporated here by reference.

INDUSTRIAL APPLICABILITY

The microcapsule containing one or more fragrances is suitable for inclusion in non-edible consumer goods products, laundry products, personal care products and cosmetic products. The microcapsule can be obtained in an economic and efficient manner by polymerizing an emulsion so that emulsion droplets are encapsulated into a subsequently cured polymeric shell.

The invention claimed is:

1. A process for the manufacture of a microcapsule comprising a perfume composition enclosed within a polymeric shell, wherein:
the perfume composition includes a fragrance, and
the polymeric shell includes in polymerized form a blend including:
i) between 40% and 70% by weight over the combined weight of compounds (I) and (II) in the blend of a compound (I) which is a combination of:
Ia) between 50% and 94.98% by weight over the weight of the combination of a neutral monomethacrylate monomer (Ia) having a solubility in water at pH 7 and 20° C. equal to, or more than 2g/100 ml,
Ib) between 5% and 50% by weight over the weight of the combination of another neutral monoethylenically unsaturated monomer (Ib), and
Ic) between 0.02% and 15% by weight over the weight of the combination of a ionized or ionizable monoethylenically unsatured monomer (Ic) which is 3-(methacryloylamino)propyltrimethylammonium chloride, and
ii) between 30% and 60% by weight over the combined weight of compounds (I) and (II) in the blend of a compound (II) which is a polyethylenically unsaturated monomer selected from the group consisting of divinylbenzene, trivinylbenzene, a $C_2$-$C_{24}$ alkyl di- or polyester of (meth)acrylic acid, a $C_2$-$C_{24}$ alkyl di- or polyamide of (meth)acrylic acid and mixtures thereof,
the process is a free radical polymerization process and includes the following steps:
a) providing an oil-in-water emulsion having an oil phase and a water phase, said oil-in-water emulsion being obtained by mixing:
a polymerization initiator,
a perfume composition including a fragrance,
an emulsifier, and
the blend,
b) triggering polymerization within the oil-in-water emulsion obtained in step a),
c) letting the polymerization propagate thereby obtaining microcapsules,
wherein the neutral monomethacrylate monomer (Ia) is selected from the group consisting of 2-hydroxyethyl methacrylate, 2-hydroxypropyl methacrylate, 3-hydroxypropyl methacrylate, glycidyl methacrylate, triethylene glycol methyl ether methacrylate; PEG300 methacrylate methyl ether, and mixtures thereof,
the another neutral monoethylenically unsatured monomer monomer (Ib) includes methyl methacrylate and/or ethyl methacrylate, and
the compound (II) includes one or more of 1,4-butane diol dimethacrylate, ethylene glycol dimethacrylate and 1,3-propylene glycol dimethacrylate.

2. The process for the manufacture of a microcapsule according to claim 1, wherein the neutral monomethacrylate monomer (Ia) includes 2-hydroxyethyl methacrylate.

* * * * *